(12) United States Patent
Des Rosiers et al.

(10) Patent No.: US 8,030,010 B2
(45) Date of Patent: Oct. 4, 2011

(54) METHOD FOR DETECTING A BIOMARKER OF OXIDATIVE STRESS IN A BIOLOGICAL SAMPLE

(75) Inventors: Christine Des Rosiers, Montreal (CA); Caroline Asselin, Montreal (CA); Bertrand Bouchard, Montreal (CA); Jean-Claude Tardif, Laval (CA); Blandine Comte, Montreal (CA)

(73) Assignee: Institut de Cardiologie de Montreal, Montreal (CA)

( * ) Notice: Subject to any disclaimer, the term of this patent is extended or adjusted under 35 U.S.C. 154(b) by 646 days.

(21) Appl. No.: 12/083,473

(22) PCT Filed: Oct. 13, 2006

(86) PCT No.: PCT/CA2006/001696
§ 371 (c)(1),
(2), (4) Date: Apr. 14, 2008

(87) PCT Pub. No.: WO2007/041868
PCT Pub. Date: Apr. 19, 2007

(65) Prior Publication Data
US 2009/0111121 A1    Apr. 30, 2009

(51) Int. Cl.
*G01N 33/53* (2006.01)
*G01N 31/00* (2006.01)

(52) U.S. Cl. ............ 435/7.21; 435/7.1; 436/1; 436/501; 436/518; 424/9.1; 424/520; 422/50; 530/300; 530/350

(58) Field of Classification Search ................ None
See application file for complete search history.

(56) References Cited

OTHER PUBLICATIONS

Gutteridge, J. M.; Halliwell, B. Free Radicals and Antioxidants in the Year 2000. A Historical Look to the Future. Ann. N. Y. Acad. Sci. 899:136-147; Apr. 2000.
Leitinger, N. Oxidized Phospholipids as Modulators of Inflammation in Atherosclerosis. Curr. Opin. Lipidol. 14:421-430; Oct. 2003.
Uchida, K. Role of Reactive Aldehyde in Cardiovascular Diseases. Free Radic. Biol. Med. 28:1685-1696; 2000.
Meagher, E. A. Treatment of Atherosclerosis in the New Millennium: Is There a Role for Vitamin E? Prey. Cardiol. 6:85-90; Jan. 2003.
Kritharides, L.; Stocker, R. The Use of Antioxidant Supplements in Coronary Heart Disease. Atherosclerosis 164:211-219; Apr. 2002.
Lonn, E.; Bosch, J.; Yusuf, S.; Sheridan, P.; et al Effects of Long-Term Vitamin E Supplementation . JAMA 293:1338-1347; Mar. 2005.
Kadiiska, et al. Biomarkers of Oxidative Stress Study II: Are Oxidation Products of Lipids, Proteins, and DNA Free Radic. Biol. Med. 38:698-710; Oct. 2004.
Moore, K.; Roberts, L. J. Measurement of Lipid Peroxidation. Free Radic. Res. 28:659-671; Jun. 1998.
Halliwell, B. et al Measuring Reactive Species and Oxidative Damage in Vivo and in Cell Culture: Br. J. Pharmacol. 142:231-255; Mar. 2004.

Zarkovic, N. 4-Hydroxynonenal As a Bioactive Marker of Pathophysiological Processes. Mol. Aspects Med. 24:281-291; Oct. 2003.
Esterbauer, et al Chemistry and Biochemistry of 4-Hydroxynonenal, Malonaldehyde and Related Aldehydes. Free Radic. Biol. Med. 11:81-128; Dec. 1990.
Awasthi, Y. C.et al Role of 4-Hydroxynonenal in Stress-Mediated Apoptosis Signaling. Mol. Aspects Med. 24:219-230; Aug. 2003.
Poli, G.; Schaur, R. J. 4-Hydroxynonenal in the Pathomechanisms of Oxidative Stress. IUBMB. Life 50:315-321; Dec. 2000.
Schaur, R. J. Basic Aspects of the Biochemical Reactivity of 4-Hydroxynonenal. Mol. Aspects Med 24:149-159; Aug. 2003.
Gueraud, F et al Enzyme Immunoassay for a Urinary Metabolite of 4-Hydroxynonenal Free Radic. Biol. Med 40:54-62; Sep. 2005.
Volkel, W et al. Conjugates of 4-Hydroxy-2(E)-Nonenal As Biomarkers of Hepatic Free Radic. Biol. Med 38:1526-1536; Feb. 2005.
Eaton, P. et al Formation of 4-Hydroxy-2-Nonenal-Modified Proteins in Ischemic Rat Heart. Am. J. Physiol 276:H935-H943; Dec. 1998.
Veronneau, M. et al Quantitative Gas Chromatographic-Mass Spectrometric Radic. Biol. Med 33:1380-1388; Aug. 2002.
Benderdour, M et al. Decreased Cardiac Mitochondrial NADP+−Isocitrate Am. J. Physiol Heart Circ. Physiol 287:H2122-H2131; Jul. 2004.
Nakamura, R et al. Probucol Attenuates Left Ventricular Dysfunction and Remodeling 106:362-367; Apr. 2002.
Toyokuni, S.; et al. Serum 4-Hydroxy-2-Nonenal-Modified Albumin Is Elevated . Redox. Signal. 2:681-685; Mar. 2000.
Salomon, R. G et al HNE-Derived 2-Pentylpyrroles are Generated. Chem. Res. Toxicol. 13:557-564; Jun. 2000.
Cabassi, A et al Effects of Chronic N-Acetylcysteine Treatment . J. Hypertens. 19:1233-1244; Feb. 2001.
Yuan, Y. V.; Kitts, D. D. Dietary (N-3) Fat and Cholesterol Alter Tissue. J. Nutr. 133:679-688; Dec. 2002.
Kobayashi, N.; et al. Oxidative Stress Promotes Endothelial Cell Apoptosis. Arterioscler. Thromb. Vasc. Biol. 25:2114-2121; Jul. 2005.
Wang, X.; et al Vascular Methylglyoxal Metabolism and the Development of Hypertension. J. Hypertens. 23:1565-1573;Apr. 2005.
Cosentino, F.et al. Tetrahydrobiopterin Alters Superoxide and Nitric Oxide Release in Prehypertensive Rats. J. Clin. Invest 101:1530-1537; Jan. 1998.
Bradford, M. M. A Rapid and Sensitive Method for the Quantitation of Microgram Quantities. Anal. Biochem. 72:248-254; Jan. 1976.
Des Rosiers C. et al. Gas Chromatographic-Mass Spectrometric Assay of Tissue. Anal. Biochem. 208:161-170; Jan. 1993.
Morrow, J. D. The Isoprostanes: Their Quantification. Drug Metab Rev. 32:377-385; Oct. 2000.
Nonaka-Sarukawa, M. et al. Increased Urinary 15-F2T-Isoprostane Concentrations in Patients. Heart 89:871-874; Feb. 2003.

(Continued)

*Primary Examiner* — Lisa Cook

(57) ABSTRACT

A method for characterizing oxidative stress. The method includes dosing a ratio of HNE-to-DHN-protein in blood; comparing the ratio of HNE-to-DHN-protein in blood to a predetermined interval of ratio values associated with a predetermined level of oxidative stress; and classifying the oxidative stress as having reached the predetermined level if the ratio of HNE-to-DHN-protein in blood is within the predetermined interval of ratio values.

16 Claims, 9 Drawing Sheets

OTHER PUBLICATIONS

Schwedhelm, E et al. Urinary 8-Iso-Prostaglandin F2Alpha as a Risk Marker in Patients. Circulation 109:843-848; Nov. 2003.

Gaut, J. P. et al. Artifact-Free Quantification of Free 3-Chlorotyrosine, 3-Bromotyrosine, and 3-Nitrotyrosine. Anal. Biochem. 300:252-259; Nov. 2001.

Shishehbor, M. H. et tal. Association of Nitrotyrosine Levels With Cardiovascular Disease and Modulation by Statin Therapy. JAMA 289:1675-1680; Apr. 2003.

Siems, W.; Grune, T. Intracellular Metabolism of 4-Hydroxynonenal. Mol. Aspects Med 24:167-175; Aug. 2003.

Doggrell, S. A.; Brown, L. Rat Models of Hypertension, Cardiac Hypertrophy and Failure. Cardiovasc. Res. 39:89-105; Feb. 1998.

Shimamoto, N. et al. Myocardial Energy Metabolism in the Hypertrophied Hearts of Spontaneously Hypertensive Rats. Basic Res. Cardiol. 77:359-7; Feb. 1982.

Diez, J.; Panizo, A. et al. Cardiomyocyte Apoptosis and Cardiac Angiotensin-Converting Enzyme in Spontaneously Hypertensive Rats. Hypertension 30:1029-1034; Apr. 1997.

Reckelhoff, J. F.; Romero, J. C. Role of Oxidative Stress in Angiotensin-Induced Hypertension. Am. J. Physiol Regul. Integr. Comp Physiol 284:R893-R912; Apr. 2003.

Srivastava, S. et al. Metabolism of Lipid Peroxidation Product, . Free Radic. Biol. Med. 29:642-651; Jun. 2000.

Esterbauer H, Schaur RJ, Zollner H. Chemistry and Biochemistry of 4-Hydroxynonenal, Malonaldehyde and Related Aldehydes. Free Radic Biol Med Dec. 1990; 11(1):81-128.

Asselin C, Bouchard B, Tardif JC, Des Rosiers C. Circulating 4-Hydroxynonenal-protein Thioether Adducts . Free Radic Biol Med 2006; 41(1):97-105 Apr. 2006.

Benderdour M, Charron G, Deblois D, Comte B, Des Rosiers C. Cardiac Mitochondrial NADP+– Isocitrate Dehydrogenase is Inactivated .J Biol Chem 2003; 278(46):45154-45159 Jun. 2003.

Benderdour M, Charron G, Comte B et al. Decreased Cardiac Mitochondrial NADP+– Isocitrate Dehydrogenase. J Physiol Heart Circ Physiol 2004; 287(5):H2122 Jul. 2004.

Chiappe De Cingolani Ge, Caldiz CI. Insulin Resistance and Glut-4 Glucose Transporter in Adipocytes From Hypertensive Rats. Metabolism 2004; 53(3):382-387 Mar. 2004.

Shimamoto N, Goto N, Tanabe M, Imamoto T, Fujiwara S, Hirata M. Myocardial Energy Metabolism in the Hypertrophied Hearts. Res Cardiol 1982; 77(4):359-7 Feb. 1982.

Tardif JC, Grégoire J, et al, for the Canadian Antioxidant Restenosis Trial (CART-1) Investigators. Circulation 2003; 107:552-558. Feb. 2003.

Slama M, Ahn J, Varagic J, Susic D, Frohlich Ed. Long-Term Left Ventricular Echocardiographic . Am J Physiol Heart Circ Physiol 2004; 286(1):H181-H185. Jan. 2004.

Kohno I, Honma H, Nakamura T, Tamura K. Comparison of Blood Pressure, Heart Rate and Activity Between Normotensive. Chronobiologia 1994; 21(1-2):45-56. May 1993.

Nakamura R, Egashira K, Machida et al. Probucol Attenuates Left Ventricular Dysfunction and Remodeling . Circulation Jul. 2002; 106(3):362-367.

Lou H, Danelisen I, Singal PK. Involvement of Mitogen-Activated Protein Kinases . Am J Physiol Heart Circ Physiol 2005; 288(4):H1925-H1930. Apr. 2005.

Sia YT, Lapointe N, Parker TG et al. Beneficial Effects of Long-Term Use of the Antioxidant Probucol in Heart Failure in the Rat. Circulation 2002; 105(21):2549-2555. Mar. 2005.

Diaz A, Bourassa MG, Guertin MC, Tardif JC. Long-Term Prognostic Value of Resting Heart Rate in Patients . Heart J 2005; 26(10):967-974 Mar. 2005.

Nakamura K, Kusano KF, Matsubara H et al. Relationship Between Oxidative Stress and Systolic Dysfunction . J Card Fail 2005; 11(2):117-123. Mar. 2005.

Ishikawa T, Esterbauer H, Sies H. Role of Cardiac Glutathione Transferase and of the Glutathione S-Conjugate Export. J Biol Chem 1986; 261(4):1576-1581. Feb. 1986.

Bhatnagar A. Electrophysiological Effects of 4-Hydroxynonenal, An Aldehydic Product of Lipid Peroxidation, on Isolated Rat . Circ Res 1995; 76(2):293-304. Feb. 1995.

Aberle NS, Picklo MJ, Sr., Amarnath V, Ren J. Inhibition of Cardiac Myocyte Contraction by 4-Hydroxy-Trans-2-Nonenal. Cardiovasc Toxicol Mar. 2004; 4 (1):21-28.

Ahn J, Varagic J, Slama M, Susic D, Frohlich Ed. Cardiac Structural and Functional Responses to Salt . Am J Physiol Heart Circ Physiol 2004; 287(2):H767-H772 Apr. 2004.

Brilla CG, Matsubara L, Weber KT. Advanced Hypertensive Heart Disease in Spontaneously Hypertensive Rats. Hypertension 1996; 28(2):269-275. Aug. 1996.

Gagnon C, Legault F, Geraldes P, Tanguay JF, Lambert C. Diverse Effects of Ace Inhibitors and Angiotensin II . Int J Cardiol 2004; 97(3):373-381. Feb. 2004.

Burcham, P. C.; Kaminskas, L. M.; Fontaine, F. R.; Petersen, D. R.; Pyke, S. M. Aldehyde-Sequestering Drugs: Toxicology 181-182:229-236; Dec. 2002.

Crabb, John W. et al Hydroxynonenal Inactives Cathepsin B. Protein Science 2002 11:831-840 Dec. 2001 USA.

METHOD FOR DETECTING A BIOMARKER OF OXIDATIVE STRESS IN A BIOLOGICAL SAMPLE

FIELD OF THE INVENTION

The present invention relates to methods for detecting a oxidative stress in a biological sample, methods of determining a cumulative record of oxidative injury, and methods of diagnosing diseases of aging, such as cardiovascular diseases, based on the presence or absence of a biomarker or a component thereof. The present invention also relates to a kit for detecting oxidative stress in a biological sample comprising a stabilizing reactant and an antibody.

BACKGROUND OF THE INVENTION

Over the past 30 years, extensive experimental evidence has accumulated supporting the implication of oxidative stress in the pathogenesis of aging and cardiovascular diseases (CVD) [1-3]. Admittedly, randomized clinical trials with "natural antioxidants" have been disappointing (HOPE, HPS, GISSI-prevention) and have led some to question the relevance of the oxidative stress hypothesis [4-6]. However, the majority of these studies did not evaluate the impact of the antioxidant intervention on the oxidative stress status, or used the highly criticized thiobarbituric acid reactive substances method (TBARS) [7-9]. This can be explained in part by difficulties encountered in validating methods to assess oxidative stress biomarkers in accessible fluids for human studies, which often require expensive and complex mass spectrometric technologies. Recently, isoprostanes have emerged as relatively good markers of oxidative stress-induced lipoperoxidation in vivo [7,9]. However, the measurement of a single biomarker is unlikely to provide a comprehensive picture of the various oxidative stress related events that may contribute to CVD progression.

One oxidative stress-related molecule that has generated considerable research interest over the past 10 years [10] is 4-hydroxy-2,3-nonenal (HNE). HNE is an aldehyde end-product generated by peroxidation of the most abundant class of n-6 polyinsaturated fatty acids [11]. Similar to free radicals, aldehydes are electrophile that react readily to nucleophilic residues of proteins, nucleic acids and lipids, but their relatively longer half-life make them candidates for the propagation of the damage to neighboring cells. Among the aldehydes, 4-hydroxy-2-alkenals such as HNE are considered the most reactive species because of their $\alpha,\beta$-double bond [11].

The interest for HNE stems not only from its potential use as a biomarker of oxidative stress-induced lipid peroxidation (LPO), but also because of accumulating evidence indicating that HNE is able to modulate signaling pathways involved in cell proliferation, apoptosis and inflammation, which are hallmarks of CVD [12, 13]. However, much remains to be learned on the role of HNE as an active biomarker of oxidative stress-related events in CVD. Because of the rapid cellular metabolism of HNE, through either reduction to 1,4-dihydroxynonene (DHN), oxidation to 4-hydroxynonenoic acid, or conjugation with glutathione [14], recent studies have highlighted the potential usefulness of measuring HNE metabolites such as dihydroxynonene mercapturic acid in urine [15] or in plasma [16], rather than free HNE.

HNE-protein adducts have also been identified. Increased levels of these adducts, assessed by immunological and gas chromatography-mass spectrometry (GCMS) methods, were reported under conditions of oxidative stress in myocardial tissues [17-20], in circulating albumin [21] and oxidized lipoproteins [22]. However, the possibility that circulating HNE-protein adducts could reflect enhanced systemic or tissue-specific oxidative stress has not been previously examined, and methods of quantifying these adducts in whole blood, plasma or other blood derivatives samples has not been previously described.

Thus, while oxidative stress has been implicated in numerous degenerative diseases of aging, including cardiovascular diseases, there is still a need to identify biomarkers of oxidative stress-related events, such as the lipid peroxidation product 4-hydroxy-2,3-nonenal (HNE) and protein thioether adducts thereof, in these diseases, and particularly in humans. In view of the above, there is a need in the industry to provide novel methods for detecting and quantifying oxidative stress in a biological sample through the use of suitable biomarkers.

SUMMARY OF THE INVENTION

In a first broad aspect, the invention relates to a method for detecting oxidative stress using a biological sample containing a biomarker of oxidative stress. The method includes obtaining a biological sample, chemically stabilizing the biomarker of oxidative stress to produce a stabilized biomarker of oxidative stress; and, after having stabilized the biomarker of oxidative stress, assessing the presence of the stabilized biomarker of oxidative stress in the sample.

Advantageously, the method allows to perform relatively complex and lengthy processes when assessing the presence of the biomarker while ensuring that levels of the biomarker inside the sample remain substantially constant during these processes.

In addition, the method is relatively easy to perform using standard laboratory procedures.

In some embodiments of the invention, the method may be performed using a kit which therefore allows to relatively effectively and simply perform the method in a relatively small number of relatively easily performed steps.

For more clarity, for the purpose of this document, the term biomarker of oxidative stress encompasses biomarkers of oxidative stress per se and biomarkers of oxidative stress-related events, such as for example and non-limitingly, biomarkers of oxidative stress-induced LPO events involved in aging and in the development and progression of cardiovascular diseases.

In some embodiments of the invention, the biomarker of oxidative stress is selected from an aldehyde-protein adduct and an aldehyde metabolite-protein adduct. For example, the metabolite-protein adduct is a metabolite-protein thioether adduct. In other examples, the metabolite is covalently bound to any suitable amino acid, such as histidine or lysine, among others, or to any other suitable substance.

In specific embodiments of the invention, the aldehyde includes 4-hydroxy-2,3-nonenal (HNE), 1,4-dihydroxynonene (DHN). In these two cases, in some embodiments of the invention, the measurable component may be selected from DHN and [$^2$H]DHN. In other embodiments the measurable component of the biomarker of oxidative stress is another metabolite produced by peroxidation of fatty acids, such as non-limitingly 4-hydroxynonenal, 4-oxononenal, 4-hydroxyhexenal and 4-oxohexenal.

In some embodiments, the quantity of the measurable component is measured using gas chromatography coupled to mass spectrometry.

In some embodiments of the invention, chemically stabilizing the biomarker in the sample includes reducing the aldehyde to its alcohol, for example by adding NaB²H₄NaBH₄ or to the biological sample. In a variant of the embodiments, reducing the aldehyde to its alcohol comprises reducing HNE to DHN and/or reducing HNE to its deuterated alcohol [²H]DHN.

In some embodiments of the invention, the biological sample contains molecules selected from HNE, HNE-protein adducts, DHN, DHN-protein adducts, metabolites of HNE, and combinations thereof.

In some embodiments of the invention, isolating the measurable component includes cleaving a protein linkage. For example, the step of cleaving a protein linkage comprises cleaving a protein thioether linkage using Raney nickel catalysis. In a specific example, the Raney nickel catalysis is conducted for about 5 to about 20 hours at a temperature of about 45° C. to about 60° C.

In some embodiments of the invention, the biological sample is selected from whole blood, blood derivatives, and combinations thereof, the blood derivatives being selected for example from plasma, albumin, and oxidized lipoprotein, among others.

In a second broad aspect, the invention relates to a method for detecting oxidative stress using a biological sample comprising obtaining a biological sample comprising a biomarker of oxidative stress; chemically stabilizing the biomarker in the sample; contacting the sample with an antibody that binds to the stabilized biomarker; and detecting the presence of the bound antibody in the sample.

In a third broad aspect, the invention relates to a method for determining a cumulative record of oxidative injury in a mammal over time, comprising: obtaining a first blood sample from a mammal at a first time point, wherein the blood sample comprises an aldehyde metabolite-protein adduct; detecting a level of oxidative stress in the first blood sample based on the quantity of the aldehyde metabolite; obtaining a second blood sample from a mammal at a second time point wherein the blood sample comprises an aldehyde metabolite-protein thioether adduct; detecting a level of oxidative stress in the second blood sample based on the quantity of the aldehyde metabolite; and determining a cumulative record of oxidative injury in the mammal using the quantities of aldehyde metabolite measured in the first and second blood samples.

In a fourth broad aspect, the invention relates to a method for assessing the risk of cardiovascular disease in a mammal, comprising: obtaining from a mammal a biological sample comprising HNE-protein adduct and DHN-protein adduct; measuring the quantities of HNE-protein adduct and DHN-protein adduct in the sample; determining a predetermined relationship between the HNE-protein adduct and the DHN-protein adduct; assessing the risk of cardiovascular disease in the mammal based on the predetermined relationship.

In a fifth broad aspect, the invention relates to a method for diagnosing a cardiovascular disease, or risk thereof, in a mammal, for example a human, comprising: obtaining from a mammal a biological sample comprising an aldehyde metabolite-protein adduct; measuring the quantity of the aldehyde metabolite-protein adduct in the sample; and diagnosing the mammal as having a cardiovascular disease, or risk thereof, if the quantities of aldehyde metabolite-protein thioether adduct present in the biological sample is greater than a predetermined threshold. For example, the cardiovascular disease or a risk factor thereof is selected from hypertension, insulin resistance, hyperglycemia, hyperlipidemia, diastolic dysfunction, fibrosis of the myocardium, and arrhythmia, cardiac hypertrophy and tachycardia. Also, for the purpose of the present specification, the term risk as it relates to cardiovascular diseases includes other diseases or conditions for which cardiovascular diseases are complications, such as diabetes, obesity, and metabolic syndrome.

In a sixth broad aspect, the invention relates to a method for diagnosing a cardiovascular disease, or risk thereof, in a mammal, comprising: obtaining from a mammal a biological sample comprising HNE-protein thioether adduct and DHN-protein thioether adduct; and diagnosing the mammal as having a cardiovascular disease, or risk thereof, if the ratio between the quantities of HNE-protein thioether adduct and DHN-protein thioether adduct is greater than a predetermined ratio.

In other embodiments of the invention, any other suitable relationship between the quantities of HNE-protein thioether adduct and DHN-protein thioether adduct is used to diagnose the cardiovascular disease or the risk thereof, such as for example a sum of these two quantities.

In a seventh broad aspect, the invention relates to a kit for detecting oxidative stress related events using a biological sample, wherein the biological sample is selected from whole blood and blood derivatives, and comprises an aldehyde, and the kit comprises: a stabilizing reactant for stabilizing the aldehyde to its alcohol; and an antibody that binds specifically to the stabilized alcohol. For example, the stabilizing reactant is suitable for converting the aldehyde to its alcohol.

In an eight broad aspect, the invention relates to a method of slowing or stopping cardiovascular disease progression in a human subject, comprising: diagnosing cardiovascular disease, or risk thereof, in a human subject; and administering a predetermined treatment known to slow or stop cardiovascular disease progression. For example, the predetermined treatment comprises administering a therapeutically effective amount of Probucol, recommending an exercise program effective for slowing or stopping cardiovascular disease progression and administering a diet effective for slowing or stopping cardiovascular disease progression, among others In a ninth broad aspect, the invention relates to a method for determining a cumulative record of oxidative injury in a mammal over time, comprising: obtaining a blood sample from a mammal, wherein the blood sample comprises an aldehyde metabolite-protein adduct; detecting a level of oxidative stress using the blood sample based on the quantity of the aldehyde metabolite present in the blood sample; and determining a cumulative record of oxidative injury in the mammal using the quantities of aldehyde metabolite measured in blood samples and a predetermined reference quantity of the aldehyde metabolite.

In a tenth broad aspect, the invention relates to a method of assessing a response of cardiovascular disease progression to a predetermined treatment in a human subject, comprising: obtaining from a mammal a biological sample comprising an aldehyde metabolite-protein adduct; measuring the quantity of the aldehyde metabolite-protein adduct in the sample; and; assessing the response of the cardiovascular disease progression to the predetermined treatment on a basis of the measured quantity of the aldehyde metabolite-protein adduct in the sample.

For example, assessing the response of the cardiovascular disease progression to the predetermined treatment includes assessing the likely outcome of a proposed treatment or assessing the progression of the cardiovascular disease in response to the predetermined treatment.

Other objects, advantages and features of the present invention will become more apparent upon reading of the following non restrictive description of preferred embodi-

DETAILED DESCRIPTION

Figure 1:
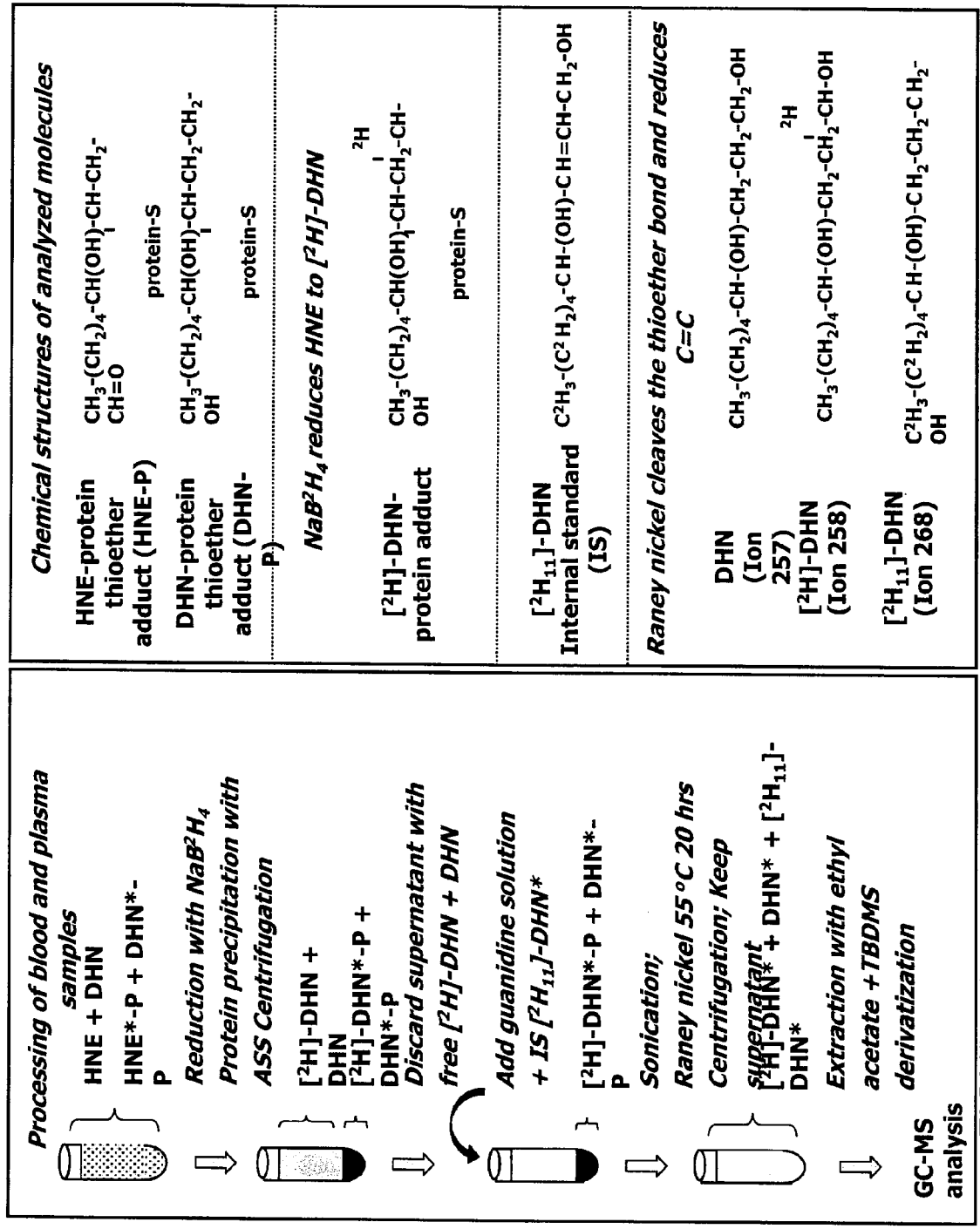
FIG. 1, in a schematic view, illustrates an overview of an experimental procedure to quantify HNE and its metabolite DHN bound to a protein via thioether linkage in blood by isotope dilution GCMS in accordance with an embodiment of the present invention, the symbol * indicating the measured molecules.

The following examples illustrate the above-mentioned method for detecting oxidative stress in a biological sample, and show that this method may be performed, for example, on an aldehyde produced through peroxidation of fatty acids. In some variants of these embodiments, stabilizing the biomarker of oxidative stress includes converting the aldehyde to its alcohol.

In some embodiments of the invention, the sample includes whole blood or a blood derivative. As used herein, the term "blood" generally refers to whole blood and blood derivatives (e.g., plasma, albumin, etc.) These samples are relatively easy to obtain and have been found to contain suitable biomarkers of oxidative stress for use in the present invention.

Some example of suitable biomarker of oxidative stress for which the proposed method are useful include: 4-hydroxy-2,3-nonenal (HNE), 1,4-dihydroxynonene (DHN), 4-hydroxynonenal, 4-oxononenal, 4-hydroxyhexenal and 4-oxohexenal. In some embodiments of the invention, these biomarkers are in the form of an aldehyde metabolite-protein adduct, such as an aldehyde metabolite-protein thioether adduct. In some variants of these embodiments, the method includes cliving the aldehyde metabolite from the aldehyde metabolite-protein thioether adduct and afterwards extracting the aldehyde metabolite-protein thioether adduct from the biological sample.

In some embodiments of the invention, a suitable analytical technique, such as for example gas chromatography, is used to assess the presence of the biomarker of oxidative stress in the sample, and in some embodiments to measure or quantify a quantity of the biomarker of oxidative stress present in the sample. In other embodiments, assessing the presence of the biomarker of oxidative stress in the sample includes contacting the sample with an antibody which binds to the stabilized biomarker of oxidative stress under conditions which allow binding of the stabilized biomarker of oxidative stress to the antibody and detecting the presence of bound antibody in the sample.

The present invention also relates to a method of slowing or stopping cardiovascular disease progression in a mammal (preferably, a human) by diagnosing cardiovascular disease, or risk thereof, according to the methods described herein, and administering a predetermined treatment known to slow or stop cardiovascular disease progression. Examples of suitable such predetermined treatments include administering a therapeutically effective amount of Probucol, recommending an exercise program effective for slowing or stopping cardiovascular disease progression, and administering a diet effective for slowing or stopping cardiovascular disease progression and administering a therapeutically effective amount of Probucol.

ANIMAL MODEL EXAMPLES

The present invention is next described by means of the following examples that were performed using animal models. The use of these and other examples anywhere in the specification is illustrative only, and in no way limits the scope and meaning of the invention or of any exemplified form. Likewise, the invention is not limited to any particular preferred embodiments described herein. Indeed, modifications and variations of the invention may be apparent to those skilled in the art upon reading this specification, and can be made without departing from its spirit and scope. The invention is therefore to be limited only by the terms of the appended claims, along with the full scope of equivalents to which the claims are entitled.

Experiments were performed to assess if circulating levels of HNE-protein adducts (i) can be assessed with precision by GCMS and (ii) vary with disease progression and aging in a model of cardiomyopathy that displays enhanced oxidative stress, namely the spontaneously hypertensive rats (SHR).

While they were performed in rats, the experiments described herein are expected to be predictive of biological effects in humans or other mammals and/or to serve as models for use of the present invention in humans or other mammals. These examples illustrate the above-mentioned methods, such as detecting oxidative stress in a biological sample, determining a cumulative record of oxidative injury, diagnosing cardiovascular diseases, and characterizing cardiovascular disease activity.

Example 1

An experiment was performed in order to quantify HNE and its inactive metabolite, 1,4-dihydroxynonene (DHN), bound to thiol protein adducts following treatment with $NaB^2H_4$ and Raney nickel. Levels of these adducts were measured in blood and plasma collected from SHR and control Wistar rats at 7, 15, 22 and 30 weeks of age. Levels of protein-bound HNE, which were quantitated with relatively good precision in the nanomolar range in blood, but not in plasma, were significantly increased by disease (SHR) and age ($p<0.0001$ for both). Compared to Wistar rats, SHR showed greater blood levels of HNE-protein adducts at 22 and 30 weeks. Levels of protein-bound DHN, which were detected in blood and in plasma, were not affected by disease or age. Collectively, the results of this study conducted in an animal model of cardiomyopathy demonstrate that changes in blood HNE-protein thioether adducts with disease progression and aging can be assessed with good precision by the described GCMS method. It is expected that this method will be useful in evaluating the occurrence and impact of oxidative stress-related events involving bioactive HNE in diseases of aging, such as cardiovascular diseases, particularly in humans.

Example 2

Another experiment was performed to assess the role of 4-hydroxynonenal (HNE) in oxidative-stress related diseases. Further to the finding of high circulating HNE-protein thioether adducts (HNE-P) in spontaneously hypertensive rats (SHR), this study aimed at correlating HNE-P with cardiac function and testing the impact of antioxidant therapy.

The lipoperoxidation inhibitor Probucol (10 mg/kg/day) or vehicle (corn oil) were administered daily (i.p.) for 4 weeks in 18-week-old SHR (9 rats/group). Cardiac functions were assessed by echocardiography and HNE-P by GCMS.

Diastolic dysfunction worsened in SHR receiving vehicle as reflected by changes ($p<0.05$) in indexes of left ventricular relaxation (increased isovolumic relaxation time) and compliance (increased E wave deceleration rate, EDR). Higher circulating HNE-P correlated with diastolic dysfunction (EDR: $R2=0.518$; $p<0.001$) and heart rate ($R2=0.225$; $p<0.05$). Probucol prevented the deterioration of diastolic function, while lowering the mean and median of circulating HNE-P by 21% and 35%, respectively. Collectively, these results support a role for HNE in the pathophysiological events linked to disease progression in SHR.

Example 3

In this next example, a method using quantitative GCMS assay of protein-bound HNE in myocardial tissues [18] was modified to enable precise and reproducible serial assessments of the small level of these adducts in blood samples. Specifically, this method quantified HNE as well as its inactive metabolite, DHN, bound to thiol proteins. However, in alternative embodiments of the invention, oxidative stress may be quantified using any other suitable substance, such as for example any other aldehyde metabolite produced by the peroxidation of fatty acids. HNE-protein thioether adducts and DHN-protein thioether adducts are considered representative of the classes of aldehyde-protein adducts and aldehyde metabolite-protein adducts.

In summary, the method involves (i) stabilisation of HNE through reduction to its deuterated alcohol [$^2$H]DHN, (ii) treatment with Raney Nickel to cleave thioether linkages, releasing protein-bound DHN and [$^2$H]DHN(HNE), and (iii) the use of a deuterated internal standard, [$^2H_{11}$]DHN that enables positive identification and quantification of the DHN chromatographic peak. As used herein, the term "[$^2$H]DHN (HNE)" refers to the stabilized deuterated alcohol of HNE. Using the modified method, the levels of circulating protein-bound HNE and DHN were assessed in 7, 15, 22 and 30-week-old spontaneously hypertensive rats (SHR) and control Wistar rats.

The SHR is a well-established model of genetic hypertension, which displays enhanced oxidative stress that responds to antioxidant treatment [23,24] as early as 4 weeks of age in the vascular wall and in the myocardium, [25-27] including accumulation of HNE-protein adducts [19]. Collectively, the results of this example demonstrate an increase in circulating HNE, but not DHN, bound to protein thiols with disease progression and aging in SHR. These results suggest the potential of these adducts as a circulating marker of oxidative stress-related events involving bioactive HNE.

Materials and Methods (Example 3)

Chemicals

Chemical, Raney Nickel, 2,6-tert-butyl-4-methylphenol (BHT), organic solvents and acids were obtained from Laboratory MAT (Quebec, Quebec, Canada), Sigma Chemical Co (St-Louis, Mo., USA), Bio-Rad (Hercules, Calif., USA) and Fisher Scientific (Nepean, Ontario, Canada) respectively. Anhydrous ammonia gas for chemical ionization (CI; 99.99% minimal purity) and helium gas (UHP) were obtained from Matheson Gas Product Canada (Montreal, Quebec, Canada). Unlabeled HNE was purchased from BIOMOL (Plymouth Meeting, Pa., USA) and the derivatization agent N-methyl-N-(tert-butyldimethylsilyl)-tri-fluoroacetamide (TBDMS) from Regis Chemical (Morton Grove, Ill., USA). Sodium borodeuteride ($NaB^2H_4$) and trans-4-hydroxy-2-nonenal-([5, 5,6,6,7,7,8,8,9,9,9-2H11] ([$^2H_{11}$]HNE) diethyl acetal were supplied by Cambridge Isotope (Andover, Mass., USA) and CDN Isotope (Pointe-Claire, Quebec, Canada). Publication [18] provides details about the preparation of stock solutions of [$^2H_{11}$]DHN and DHN, as well as determination of their concentration by measurement of HNE solution absorbance at 223 nm, prior to reduction with $NaBH_4$. All aqueous solutions were prepared with water purified by milli-Q system (Millipore, St-Laurent, Quebec, Canada). All other reagents were of analytical grade.

Animals and Sample Collection

Animal experiments were approved by the local animal care committee in compliance with the guidelines of the Canadian Council on Animal Care. Rats were housed for at least 7 days in a 12-h light/12-h dark cycle facility with unlimited access to water and standard chow prior to sacrifice. Male SHR and age-matched control Wistar rats (Charles River, St-Constant, Quebec, Canada) were sacrificed at 7 (n=11), 15 (n=13), 22 (n=8) and 30 (n=8) weeks of age. Body weights at sacrifice were, respectively, 187±13, 332±22, 375±9 and 406±15 g for SHR and 239±28, 442±31, 533±32 and 612±15 g for Wistar rats. Blood was collected under sodium pentobarbital anesthesia (65 mg/g, intraperitoneal; MTC Pharmaceuticals) by cardiac puncture with a 10-ml syringe pre-coated with EDTA (10.8 mg) and BHT (0.0496 mg). A sample of whole blood (500 µl) was immediately frozen in liquid nitrogen. The remaining volume was centrifuged at 1,500 g for 10 min and the collected plasma sample was also immediately frozen in liquid nitrogen. All samples were kept at −80° C. until analysis.

Analytical Procedures

The procedure for sample preparation and GCMS analysis of HNE- and DHN-protein adducts in blood and plasma is outlined in FIG. 1. The previously described method for detecting protein-bound HNE in myocardial tissues [18] was modified to increase its sensitivity 20-fold to enable detection of the lower quantity of protein-derived HNE and DHN found in blood and plasma samples, as well as to improve its reproducibility and ruggedness. Routinely, blood and plasma samples (400 µl) were individually mixed with 1 ml of cold buffer (pH 7.0) containing 39 mM Hepes, 0.4 mM EDTA and 0.9 mM BHT to minimize lipid peroxidation during processing, immediately treated with 200 µl 1 M $NaB^2H_4$ to reduce HNE to its chemically stable alcohol derivative [$^2H$]DHN, and left on ice for 30 min.

Then, proteins were precipitated by addition of saturated sulfosalicylic acid (final concentration 8% (v/v)). After 30 min on ice, samples were centrifuged at 5,000 g for 45 min. The protein pellets were washed with 3 ml methanol:chloroform (2:1) to remove lipids and with waterthree times, resuspended into 500 µl of solution containing 8 M guanidine, 13 mM Tris (pH 7.2) and 133 mM EDTA, and spiked with 0.1 nmol of deuterated internal standard [$^2H_{11}$] DHN. Solutions were sonicated (3×20 sec) to optimize protein dissolution, and 1 ml of water was added before treatment with 2.5 g of Raney Nickel catalysis for 20 h at 55° C. Since this treatment cleaves thioether linkages and reduces C═C bonds, free saturated derivative of [$^2H$]DHN and DHN are released into solutions and are subsequently processed for GCMS analysis. Hence, following centrifugation, twice at 1700 g for 3 min at room temperature, the aqueous supernatants were brought to pH<2 with concentrated HCl, saturated with sodium chloride and extracted two times with 10 ml of ethyl acetate by vortexing 3 min. The extracts were evaporated under nitrogen and the residues were treated with 50 ml of TBDMS. For optimal derivatization, samples were heated during 4 hours at 90° C. Protein determination was achieved by the Bradford assay [28] using bovine serum albumin (Fraction V, Sigma) as standard. The recovery of proteins after precipitation with saturated sulfosalicylic acid was evaluated to be >99% based on protein determination in the supernatant.

GCMS Assays

All samples were performed on bench-top standard equipment form Agilent Technologies consisting of model 6890N Gas chromatograph coupled to 5973 Mass Selective Detector operated in the PCI mode using ammonia as the reagent gas, and equipped with a model 7683 Series injector. Injections (1 µl) were performed at 300° C. in pulsed-splitless mode (injection pulse pressure 35 psi). The carrier gas was high-purity helium at a constant flow-rate of 0.7 ml/min. An Agilent Technologies-type HP-5 capillary column (50 m×0.2 mm inner diameter×0.5 µm phase thickness) was used under the following conditions: 170° C. for 1 min, increased by 10° C./min until 210° C., 5° C./min until 280° C. and then by 20° C./min until 325° C. At the end of each run, the temperature was kept at 325° C. for 8 min to clean the column. The GCMS transfer line was at 300° C., the ion source and quadrupole temperatures were at 300° C. and 176° C., respectively. The electron energy and emission current was at 65 eV and 242 mA respectively, and ammonia pressure (10 torr) was maintained at 1 ml/min. The following ion set was monitored with a dwell time of 50 ms per ion for the analysis of DHN, [$^2H$]DHN (reduced HNE), and the internal standard [$^2H_{11}$] DHN at m/z 257, 258 and 268, respectively. Alternatively one could also monitor the ion set 389, 390 and 400, which corresponds to the M+H+ ion, using a lower ion source temperature [18], to confirm peak identity. However, in this example, a better MS signal was obtained using the former ion.

Quantities of DHN- and HNE-protein adducts that are reported in this study represent average of duplicate or triplicate sample injections. GC peak areas for the DHN and [$^2H$]DHN peaks, determined by computer integration, were corrected for light isotopic impurities of the internal standard [$^2H_{11}$]DHN and for naturally occurring heavy isotopes, respectively. Quantities of DHN and [$^2H$]DHN were calculated using corrected areas and from the quantity of internal standard added to each sample as previously described [29].

Method Validation

The following method validation parameters were determined. (i) Accuracy was calculated from: [1-(GCMS measured quantity/standard quantity)]×100. (ii) Precision orthe relative standard deviation (RSD) was calculated from: SD *100/mean. (iii) The limit of detection (LOD) represents the minimum quantity of standard DHN solution that can be processed and assessed with good accuracy and precision. (iv) The limit of quantification (LOQ) represents the minimum quantity of protein-derived DHN and HNE that can be assayed in blood or plasma samples with an appreciate precision. It was determined by analyzing increasing volume (50, 100, 250, 400 and 500 µl) of blood and plasma in duplicate samples. (v) The intra- and inter-assay RSD for the GCMS analysis were determined by injecting one sample eight times in one day and (ii) five samples on three different days, respectively. Intra- and inter-assay RSD for the whole analytical procedure were determined by processing (a) on the same day, nine samples obtained from a pooled blood sample collected from Wistar rats, and (b) on three different days, blood samples collected from five Wistar rats and frozen in separate aliquots. Inter-assay RSD values were also obtained for the analyses of four different blood samples from Wistar rats before and after 9 months of sample freezing at −80° C. Finally, to test the specificity of the signal corresponding to HNE, blood samples were pooled and divided 6 fractions, 3 fractions were treated with NaBH4 and 3 with $NaB^2H_4$.

Statistical Analysis

Data are expressed as mean±SD or SE. The two-way ANOVA was used to test for significant differences in the effect of (i) disease development and progression in SHR, (ii) age, and (iii) the interaction of disease and age, followed by a Bonferroni multiple-comparison post-test.

Results (Example 3)

Method Validation

Figure 2:
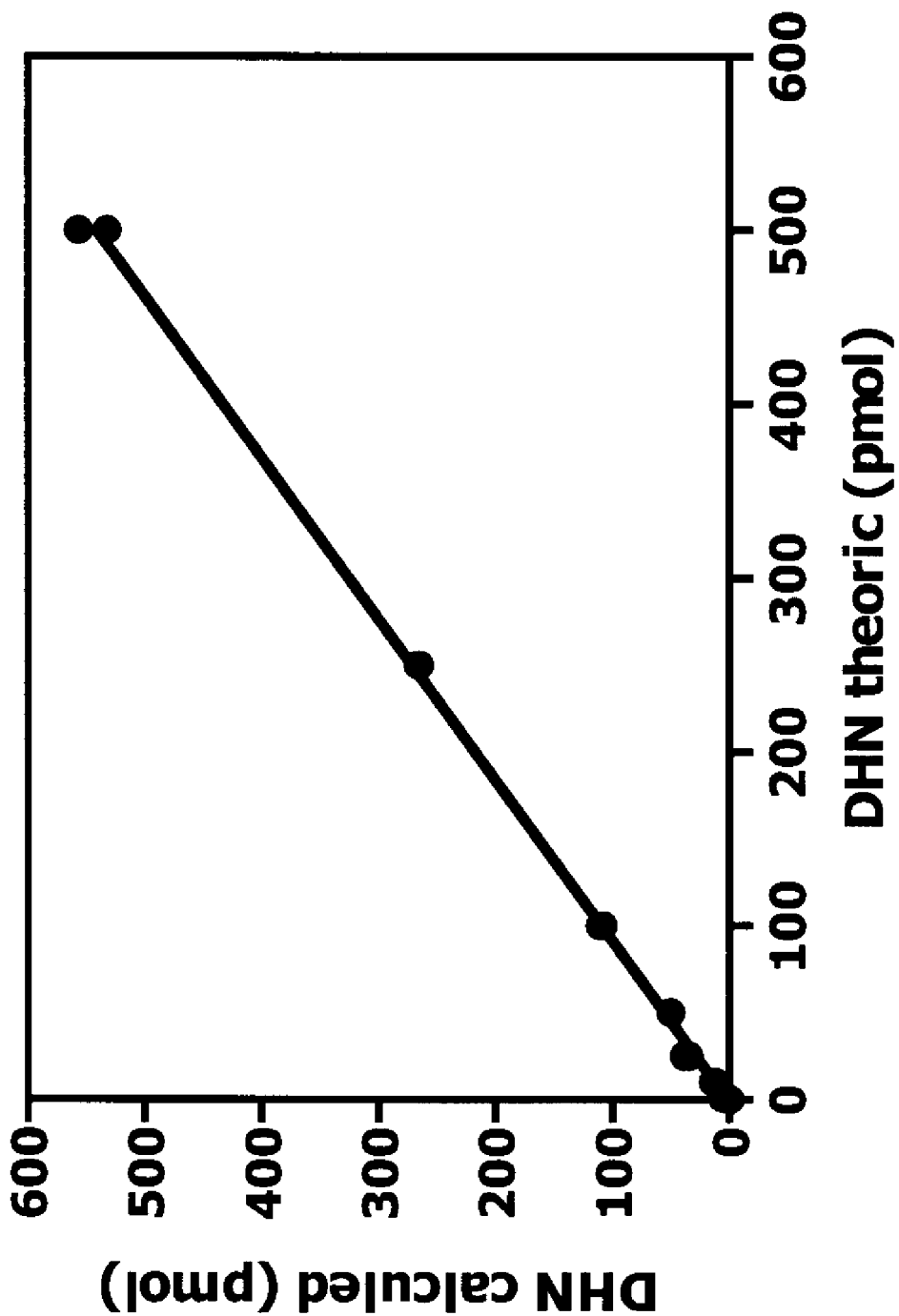
FIG. 2, in a X-Y graph, illustrates a standard curve obtained for DHN demonstrating the linearity of the GCMS assay; DHN standard solutions of 1 to 500 pmol were processed for analysis in duplicate; a regression line is shown including the 95% confidence intervals (slope: 1.079±0.009; y-intercept: 2.2±1.6; $p<0.0001$; $R2=0.999$).

The GCMS method depicted in FIG. 1 was evaluated for the following parameters: LOD, LOQ, precision, reproducibility, and robustness. The limit of detection (LOD) determined with DHN standard solutions, was estimated to be 50 μmol, based on the poor accuracy obtained when analyzing quantity below 50 μmol, between 16 and 76%, compared to values >90% for quantity between 50 and 500 μmol (Table 1). The calibration curve was linear in this range of DHN concentration tested (FIG. 2), with RSD values <4%.

TABLE 1

Calibration data obtained for a GCMS assay of DHN standard solutions used in a method for detecting a biomarker of oxidative stress in a biological sample in accordance with an embodiment of the present invention.

| Quantity added (pmol) | Quantity measured (pmol; mean ± SD) | Accuracy (%) | Precision (RSD %) |
|---|---|---|---|
| 1 | 6.3 ± 0.7 | 16 | 12 |
| 10 | 13.1 ± 0.8 | 76 | 6.3 |
| 25 | 37.1 ± 2.9 | 67 | 7.8 |
| 50 | 50.7 ± 0.3 | 99 | 0.6 |
| 100 | 110 ± 2 | 91 | 1.8 |
| 250 | 266 ± 0.4 | 94 | 0.2 |
| 500 | 545 ± 17 | 92 | 3.2 |

Standard solutions of 1 to 500 μmol DHN were processed for GCMS assay in duplicate.

Figure 3:
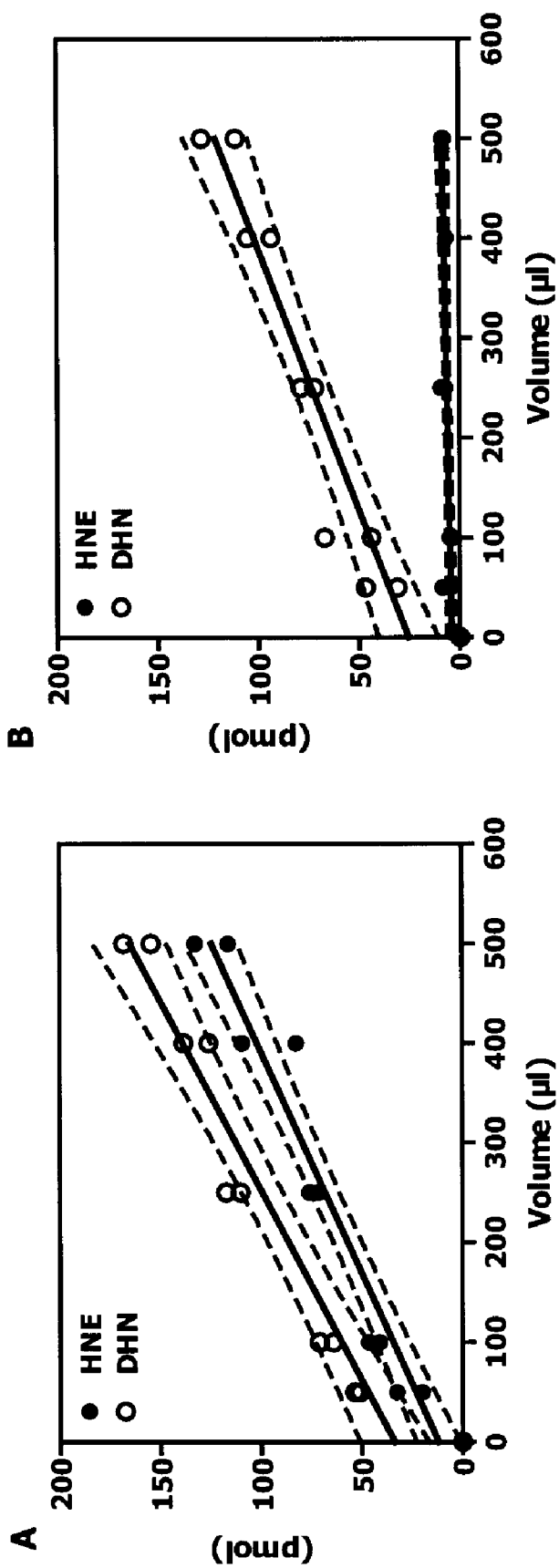
FIG. 3, in X-Y graphs, illustrates calibration curves obtained for the GCMS assays of protein-derived HNE and DHN in increasing volumes of (panel A) blood and (panel B) plasma, the assays having been performed in accordance with an embodiment of the present invention; samples for the various volumes were processed for analysis in duplicate; regression lines with 95% confidence intervals are shown: (panel A) HNE: slope=0.23±0.02, y-intercept: 12±5, $R2=0.944$, $p<0.0001$; DHN: slope=0.26±0.03, y-intercept: 34±8, $R2=0.922$, $p<0.0001$; and (panel B) HNE: slope=0.008±0.004, y-intercept: 4±1, $R2=0.346$, NS; DHN: slope=0.19±0.02, y-intercept: 26±7, $R2=0.891$, $p<0.0001$.

As for the method LOQ, there was a linear relationship for the analysis of protein-bound HNE and DHN in whole blood (FIG. 3A), although the positive values for the y-intercepts, which fall in the LOD range, indicated a constant bias. Hence, the y-intercept values were taken as background and subtracted from all calculated experimentally determined values. A similar result was obtained for the analysis of protein-bound DHN in plasma (FIG. 3B), but values for protein-bound HNE in plasma felt below the method LOD. A good precision (RSD<12%) was obtained for the measured values of protein-bound HNE and DHN in blood, and DHN in plasma. The LOQ of the method was estimated at 60 pmol, corresponding to about 250 μl samples. However, in routine applications, the practical method LOQ chosen was ≧80 pmol, corresponding to 400 μl samples, to ensure optimal precision.

Figure 4:
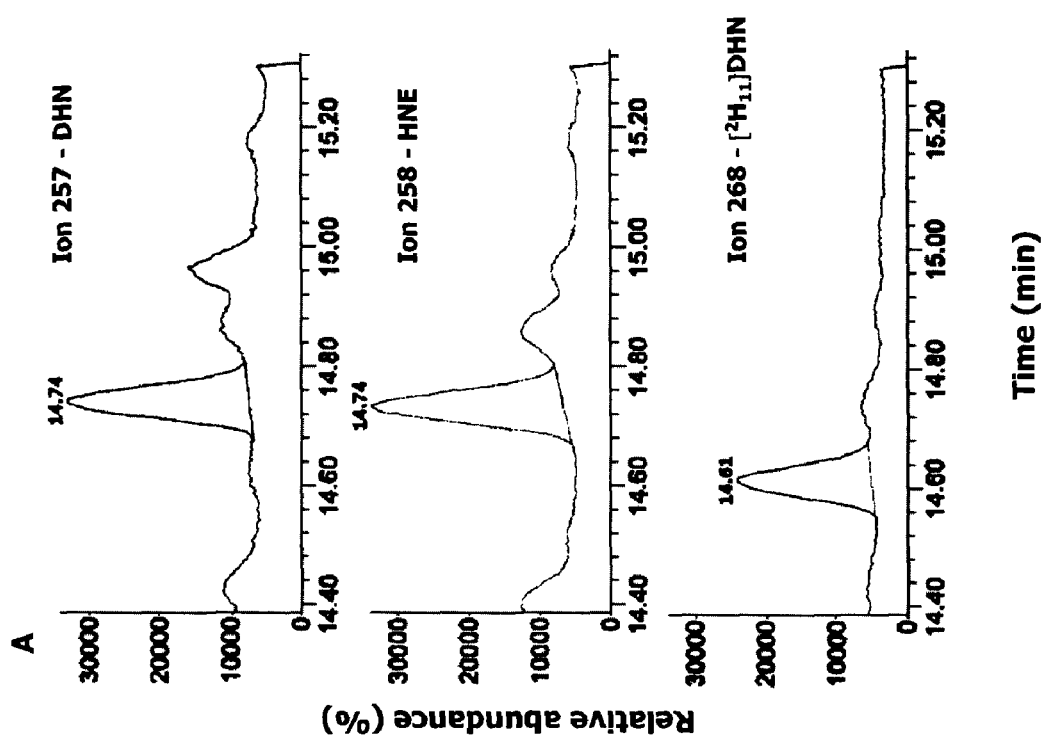
FIG. 4, in X-Y graphs, illustrates selected ion monitoring chromatograms of ion m/z 257 (upper chromatograms), m/z 258 (middle chromatograms) and m/z 268 (lower chromatograms) corresponding to DHN, HNE, and the deuterated internal standard $[^2H_{11}]$DHN, respectively, obtained from the processing of a representative blood sample from 30 week-old spontaneously hypertensive rats (SHRs), which was processed in accordance with an embodiment of the present invention.
Figure 5:
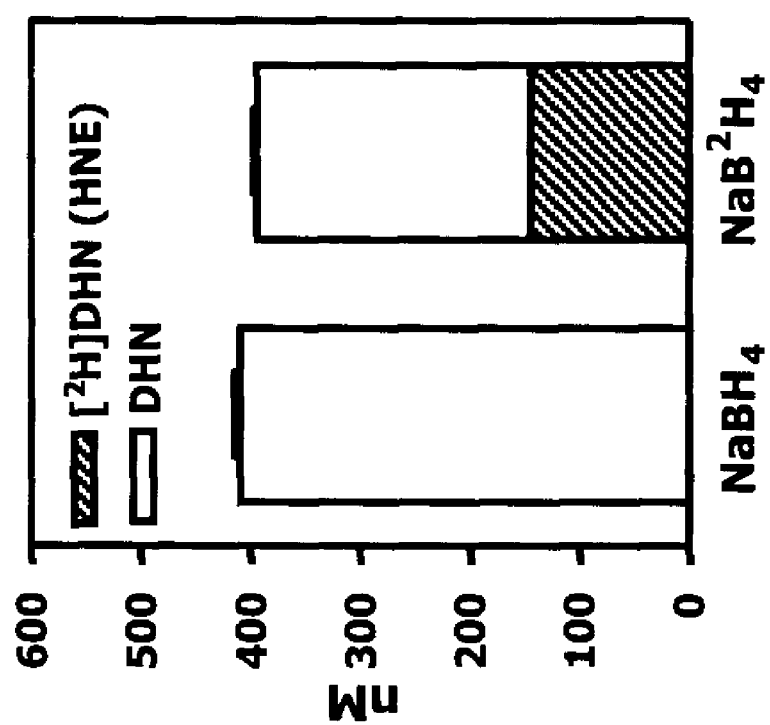
FIG. 5, in a bar chart, illustrates the specificity of the HNE signal obtained using a method in accordance with the present invention, the specificity being demonstrated by the treatment of parallel blood samples with $NaBH_4$ and $NaB^2H_4$, which converts HNE to DHN (ion m/z 257) and $[^2H]$DHN (ion m/z 258), respectively; there was no detection any quantity of protein-derived HNE signal following $NaBH_4$ treatment, while the measured quantity of protein-derived DHN corresponded to that of DHN plus HNE assessed following treatment with $NaB^2H_4$; Data are means±SE of triplicate determinations.

Table 2 summarizes the repeatability data for the assay of protein-bound HNE and DHN in 400 μl blood. FIG. 4 shows typical SIM chromatograms of a representative 400-μl blood sample collected from 30-week-old SHR. The intra- and inter-assay RSD were ≦11% for the GCMS analysis of whole blood samples and ranged between 10 and 20% for the whole method. Finally, the following additional data support also the robustness of our method. First, RSD values obtained for the analyses of protein-bound HNE and DHN in blood samples from Wistar rats after 9 months indicate the stability of these adducts upon sample freezing at −80° C. (Table 2). Second, the specificity of the HNE signal (ion 258) was demonstrated by treatment of parallel samples with $NaBH_4$ and $NaB^2H_4$, which converts HNE to DHN (ion m/z 257) and [$^2$H]DHN (ion m/z 258), respectively. While we did not detect any quantity of protein-derived HNE signal (ion 258) following $NaBH_4$ treatment, the measured quantity of protein-derived DHN (ion m/z 257) corresponded to that of DHN plus HNE assessed following treatment with $NaB^2H_4$ (FIG. 5).

TABLE 2

Summary of reproducibility data for the GCMS assay of HNE- and DHN-protein thioether adducts in 400 μl blood in accordance with an embodiment of the present invention.

| | GC-MS INJECTION | | GC-MS METHOD | | |
|---|---|---|---|---|---|
| Measured compound | Intra-assay (n = 8) RSD (%) | Inter-assay (n = 5) RSD ± SD (%) | Intra-assay (n = 9) RSD (%) | Inter-assay (n = 4) RSD ± SD (%) | 9 months of freezing (n = 4) RSD ± SD (%) |
| HNE | 3.4 | 7.9 ± 6.0 | 11 | 20 ± 9 | 26 ± 15 |
| DHN | 8.2 | 11 ± 6 | 11 | 10 ± 6 | 14 ± 6 |

The intra- and inter-assay RSD for the GCMS injection and processing of whole blood samples on different days were determined as described in Materials and Methods. Data are means±SD of 4-9 separate determinations, as indicated.

Circulating Levels of HNE- and DHN-Protein Adducts in SHR and Wistar Rats

Figure 6:
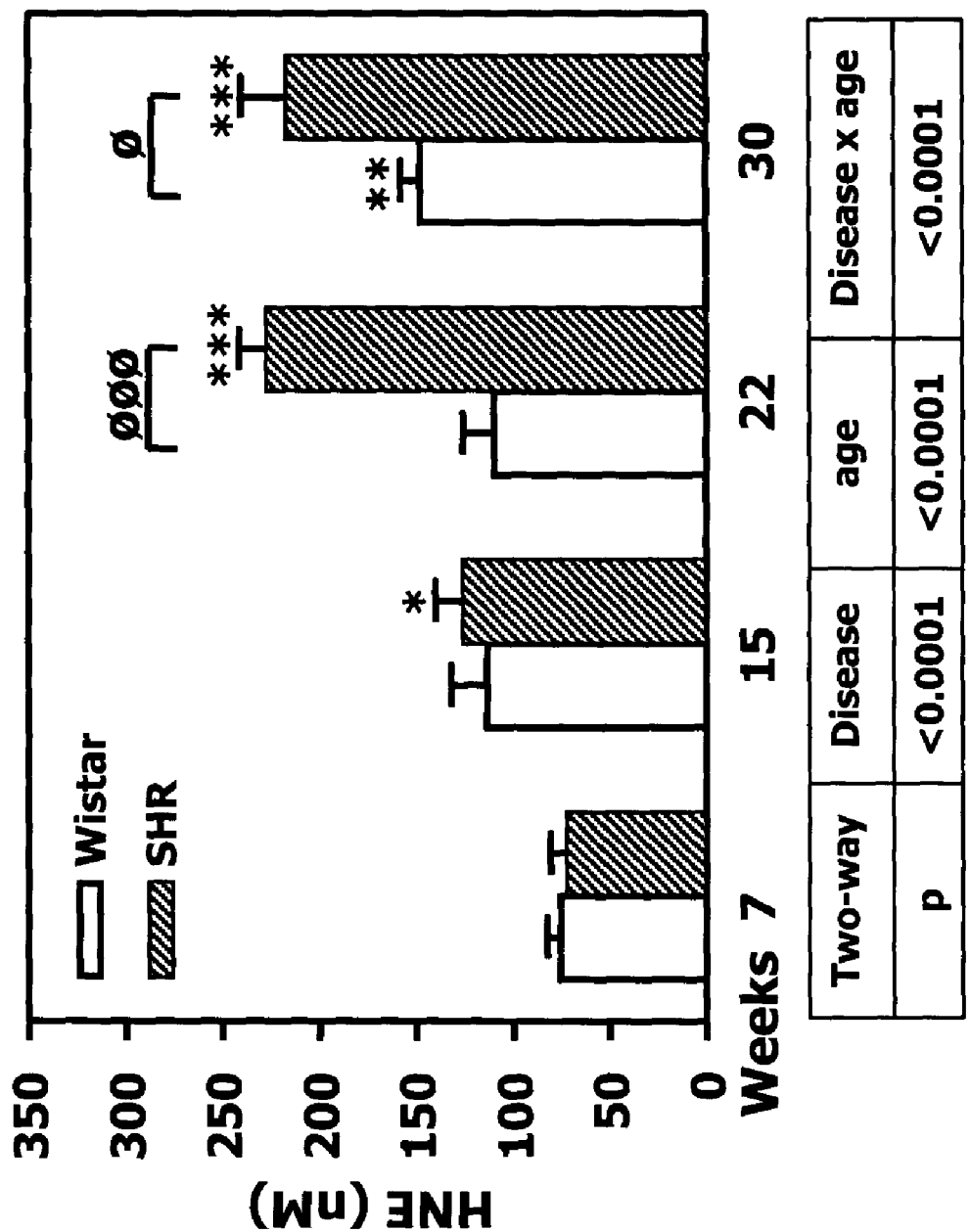
FIG. 6, in a bar chart, illustrates levels of HNE-protein thioether adducts in blood of SHR and Wistar rats at various ages obtained using a method in accordance with an embodiment of the present invention, samples (400 ml) of blood collected from 7-, 15-, 22- and 30-wk-old SHR and Wistar rats having been processed for GCMS analysis; Data are means±SE of 8-13 rats; statistics: Two-way ANOVA followed by the Bonferroni multiple-comparison post-test; effect of disease: SHR versus Wistar, øøp<0.001; øp<0.05 Effect of age, vs. 7 weeks, *p<0.05, p<0.01, *p<0.001.

FIG. 6 present data on the levels of protein-bound HNE assessed in blood collected from SHR and Wistar rats at various ages. According to the two-way ANOVA, blood levels of HNE-protein adducts were significantly increased with disease progression and age. Compared to Wistar rats, SHR showed significantly greater blood levels of HNE-protein adducts starting at 22 weeks. The observed differences in the circulating levels of protein-bound HNE with age, or between SHR and Wistar rats, cannot be attributed to variations in blood protein levels, which were similar at all times (between 230 and 274 mg/ml). In contrast to protein-bound HNE, levels of protein-bound DHN in blood (FIG. 7) or in plasma (data not shown) did not vary with disease or age.

Discussion

In this study, a GCMS method for relatively precise quantitation of HNE- and DHN-bound to circulating thiol-containing proteins was validated. The method involves stabilisation of HNE through reduction to its deuterated alcohol [$^2$H]DHN, treatment of samples with Raney Nickel, and the use of a deuterated internal standard, [$^2$H$_{11}$]DHN. The proposed method was characterized for the following parameters: LOD, LOQ, precision, reproducibility, and robustness. As currently described, one technician can process about 80-100 samples per week. The variation between different assays (10-20%) is smaller than that between subjects (30-40%). Further, the precision observed in the LOQ determination compares well with GC/LC-MS assay of plasma isoprostanes [30] or nitrotyrosine [31], which are used as markers of oxidative and nitrosative stress, respectively. Moreover, while the stability of LPO-derived products in biological samples has often been considered a major problem [32], we found that levels of HNE- and DHN-protein adducts were little affected by storage of samples for 9 months at −80° C. (Table 2). Although this may be attributed to the greater stability of these protein adducts compared to free HNE, Spies-Martin et al (2002) reported similar levels of free HNE in tissue samples before and storage for 22 months at −80 C [33]. Nevertheless, we consider relatively important to either freeze or process immediately all collected blood samples in EDTA as well as to rapidly treat samples with $NaB^2H_4$ to stabilize HNE.

In this study, the modified GCMS method was successfully applied to the analysis of circulating HNE- and DHN-protein adducts in rats. HNE-protein adducts were detected in blood, but not in plasma samples. This finding concurs with the observations of Kinter et al. [36] who assessed HNE free or bound in Schiff base residues as an oxime derivative by GCMS. Further, Oliver et al. demonstrated the accumulation of oxidatively modified proteins in erythrocytes [37]. Finally, HNE, which is predominantly detected in biomembranes rather in the aqueous phase [14], reacts rapidly in vitro with the sulfhydryl group of cysteine residues from erythrocyte membrane proteins to form Michael-type adducts. Little is known about the half-life of blood HNE-modified proteins, but it is likely to be greater than free HNE. In fact, HNE-modified proteins may reflect the flux, rather than the circulating levels, of this LPO product [22]. This cumulative record of oxidative injury may provide a sensitive measure of oxidative stress-related events involving bioactive HNE. By analogy, glycosylated hemoglobin reflects long term glycemic control [38].

The concentration of protein-bound HNE that was measured in blood samples varied between 0.07-0.22 mM. These values fall in the range of concentrations reported for plasma free HNE (0.026-0.85 mM) [32,33,36,39], but are lower than those for HNE-derived 2-pentylpyrroles (8-35 mM) [22], while greater than those for isoprostanes (35-356 pg/ml) [40-42] or nitrotyrosine (2-5 nM) [31,43,44]. Based on an average protein content of 250 mg/ml and assuming an average protein molecular mass of 30,000, a concentration of 0.07-0.25 mM of protein-bound HNE in blood implies that between 0.0008-0.003% of blood proteins is modified by HNE. This percentage is lower than the one that was calculated from the previously determined levels of HNE-protein adducts in ischemic hearts (approximately 0.025%)[18]. However, it is compatible with the observed 1 to 8% protein modification observed in vitro when mammalian cells are incubated with 100 µM HNE [45], if one takes into account that circulating free HNE concentration is <1 µM.

Figure 7:
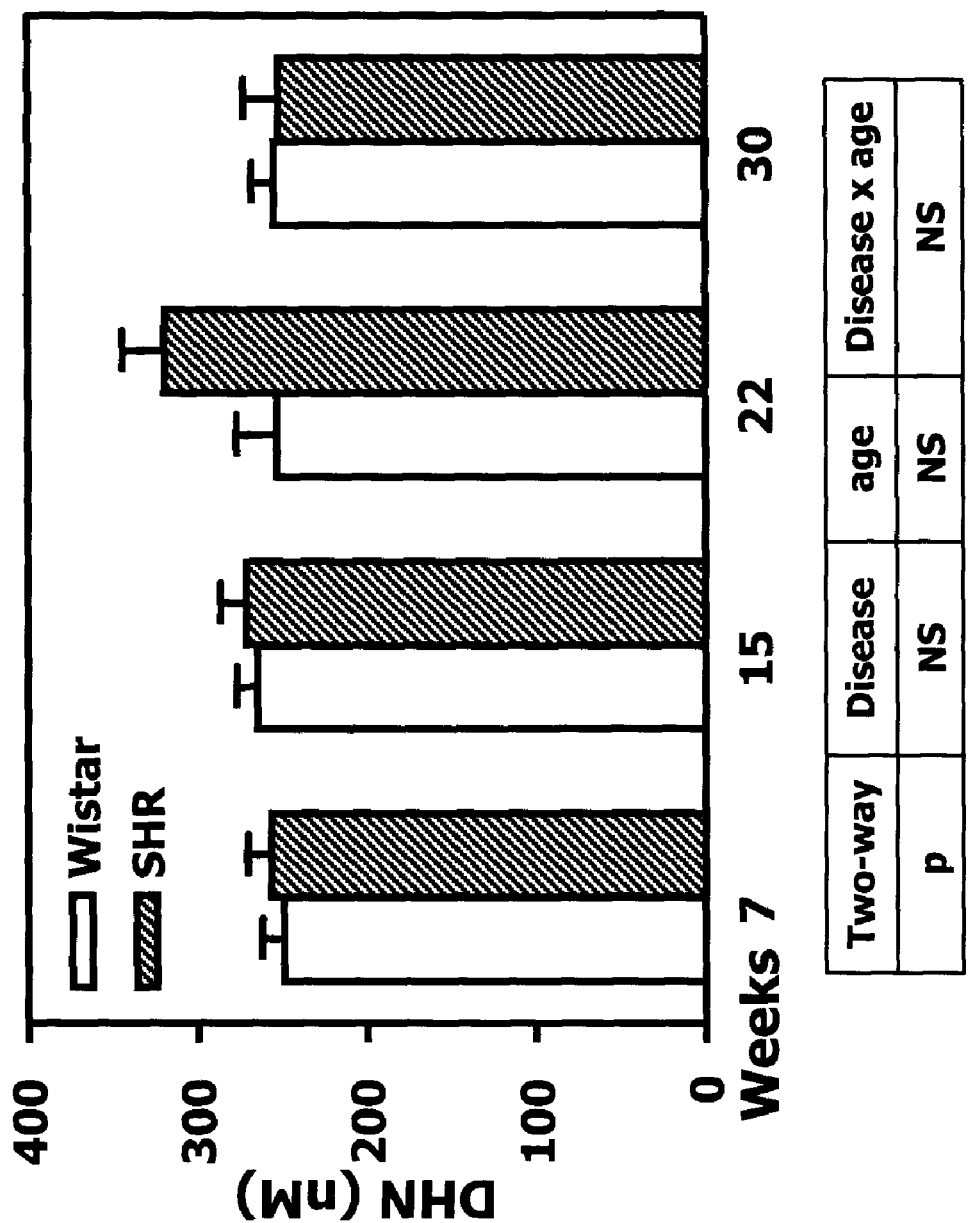
FIG. 7, in a bar chart, illustrates levels of DHN-protein thioether adducts in blood of SHR and Wistar rats at various ages, the levels having been obtained using a method in accordance with an embodiment of the present invention; data are means±SE; statistics: NS; Two-way ANOVA followed by the Bonferroni multiple-comparison post-test.

Results from this study demonstrate increased levels of HNE-protein adducts in blood of SHR with disease progression and aging, a finding that suggests that these protein adducts are circulating biomarker of oxidative stress-related events involving bioactive HNE in this animal model. The SHR develops hypertension and left ventricular hypertrophy between 9 and 14 weeks [46,47]. At 15 weeks, the hypertrophy is compensated, while at 30 weeks, SHR exhibit increased cardiomyocyte death by apoptosis, the latter being linked to transition from compensated to decompensated hypertrophy [48]. The increase in circulating HNE-protein adducts found in SHR concurs with the presence of enhanced oxidative stress, which was documented as early as 4 weeks of age [27]. This raise has been attributed to increased superoxide anion production due to dysfunctional nitric oxide synthase activity [27] and/or angiotensin II-stimulated NAD(P)H oxidase activity in the vascular wall [49]. A persistently greater accumulation of myocardial HNE-protein adducts in SHR compared to control rats was also found, an effect that was affected by disease progression and age [19]. The fact that the increase in HNE-protein adducts in blood occurred at a later age than in the vascular wall or in the heart (22 versus 7 weeks) may suggest that in SHR, HNE formation occurs predominantly at an intracellular site. A greater concentration of HNE-protein adducts in tissues compared to interstitial fluids was reported by others [13], suggesting that accumulation of circulating HNE-protein adducts may reflect the global status of HNE production versus its detoxification in all body tissues and organs. In this regard, it was found that circulating levels of protein-bound DHN, which may originate from the enzymatic reduction of HNE-protein adducts by the aldose reductase [50], were not affected by disease or age (FIG. 7). Hence, the increase in the proportion of HNE-to-DHN bound to circulating thiol proteins suggest an imbalance between HNE production versus detoxification with disease progression and aging, in the favor of the former process.

In summary, the GCMS method herein described and characterized quantifies HNE-protein thioether adducts in blood with relatively good precision and reproducibility. Using this method, it was showed that circulating HNE-protein adducts increase with disease progression and age in SHR, an animal model of cardiomyopathy that displays enhanced oxidative stress [19,26]. Collectively, the results of this study suggest the potential usefulness of HNE-protein thioether adducts measured in whole blood as marker of oxidative stress-induced LPO events involving bioactive HNE in heart diseases and aging.

It is hypothesized that a kit for assessing the presence of a biomarker of oxidative stress in a sample could be used instead of the above-described method. Also, it is hypothesized that alternative method may be used to detect a biomarker of oxidative stress. In an example of such a method, the method includes contacting the sample with an antibody which binds to the stabilized biomarker of oxidative stress under conditions which allow binding of the stabilized biomarker of oxidative stress to the antibody and detecting the presence of bound antibody in the sample.

Example 4

A series of studies was conducted in spontaneously hypertensive rats (55-57), which provided the basis for exploring in vivo the potential link between HNE and cardiac function. The SHR is a well-established model of genetic hypertensive cardiomyopathy associated with insulin resistance (58). It develops hypertension and left ventricular hypertrophy between 9 and 12 weeks (59). At 15 weeks, the hypertrophy is compensated and functional symptoms of decompensation appear after 18-24 months of age. The SHR displays enhanced oxidative stress in the vascular wall (60), which responds to antioxidant treatment (61). Further to the finding of an accumulation of myocardial HNE-protein adducts in SHR starting at 7 weeks (57), a GCMS method was validated to quantify HNE-protein thioether adducts in blood (HNE-P) and found relatively high circulating HNE-P in SHR starting at 22 weeks of age (55). Hence, in this example, circulating HNE-P was correlated with cardiac function in vivo and tests were performed to evaluate the impact of an antioxidant treatment with Probucol (62).

Method (Example 4)

Animals

Experiments were approved by the local animal care committee in compliance with guidelines of the Canadian Council on Animal Care. After one week of acclimatization, 18-wk-old male SHR (Charles River, St. Constant, Canada) were randomly assigned to receive daily an intraperitoneal injection of 10 mg kg-1 body weight Probucol (P) dissolved in corn oil or the vehicle (V). Body weight was assessed daily. At 22 weeks of age, rats were sacrificed. Blood was collected under ketamine/xylazine anaesthesia (87.5 mg/12.5 mg·kg-1, i.m.) by jugular vein puncture with a 5-ml syringe precoated with EDTA (10.8 mg) and butylated hydroxytoluene (0.0496 mg), and immediately frozen in liquid nitrogen.

Blood Pressure and Cardiac Function.

Non-invasive systolic arterial pressure was measured and transthoracic echocardiographic evaluation was performed at baseline and at the end of treatment, using the tail-cuff method and S12 phased-array transducer with a standard echocardiographic system (Sonos 5500, Hewlett-Packard, Andover, Mass.) under isoflurane anesthesia, respectively. We herein report echocardiographic parameters reflecting diastolic function only, since systolic function was reported to be unchanged in SHR at 18-22 weeks (13). In the apical 4-chamber view, transmitral E wave deceleration time (EDT) and deceleration rate (EDR) were measured using pulsed-wave Doppler, and mitral propagation velocity (Vp) was studied through color M-mode spectrum. LV isovolumic relaxation time (IVRT) was measured in the 5-chamber view using continuous-wave Doppler and corrected (IVRTc) with the R—R interval taken from simultaneously recorded ECG. M-mode at the aortic valve level in the parasternal long axis view was used to measure left atrial (LA) dimensions in both cardiac diastole (LADd) and systole (LADs), from which we calculated LA fractional shortening (LAFS). The average of three consecutive cardiac cycles was used for each measurement.

Circulating HNE-P. HNE-P was quantified in 400 µl whole blood collected at the end of treatment, by GCMS as described in Example 1.

Data Presentation and Statistical Analysis.

Data are means±SEM. Values for the various parameters measured (body weight, systolic blood pressure and cardiac functions) are reported as percentages of pre-treatment values. Statistical significance of differences between and within groups (before vs aftertreatment) was assessed using unpaired and paired t-tests, respectively. Correlation coefficients were calculated by linear regression analysis. A value of $p \leq 0.05$ was considered significant.

Results (Example 4)

Hemodynamics and Cardiac Function.

Figure 9:
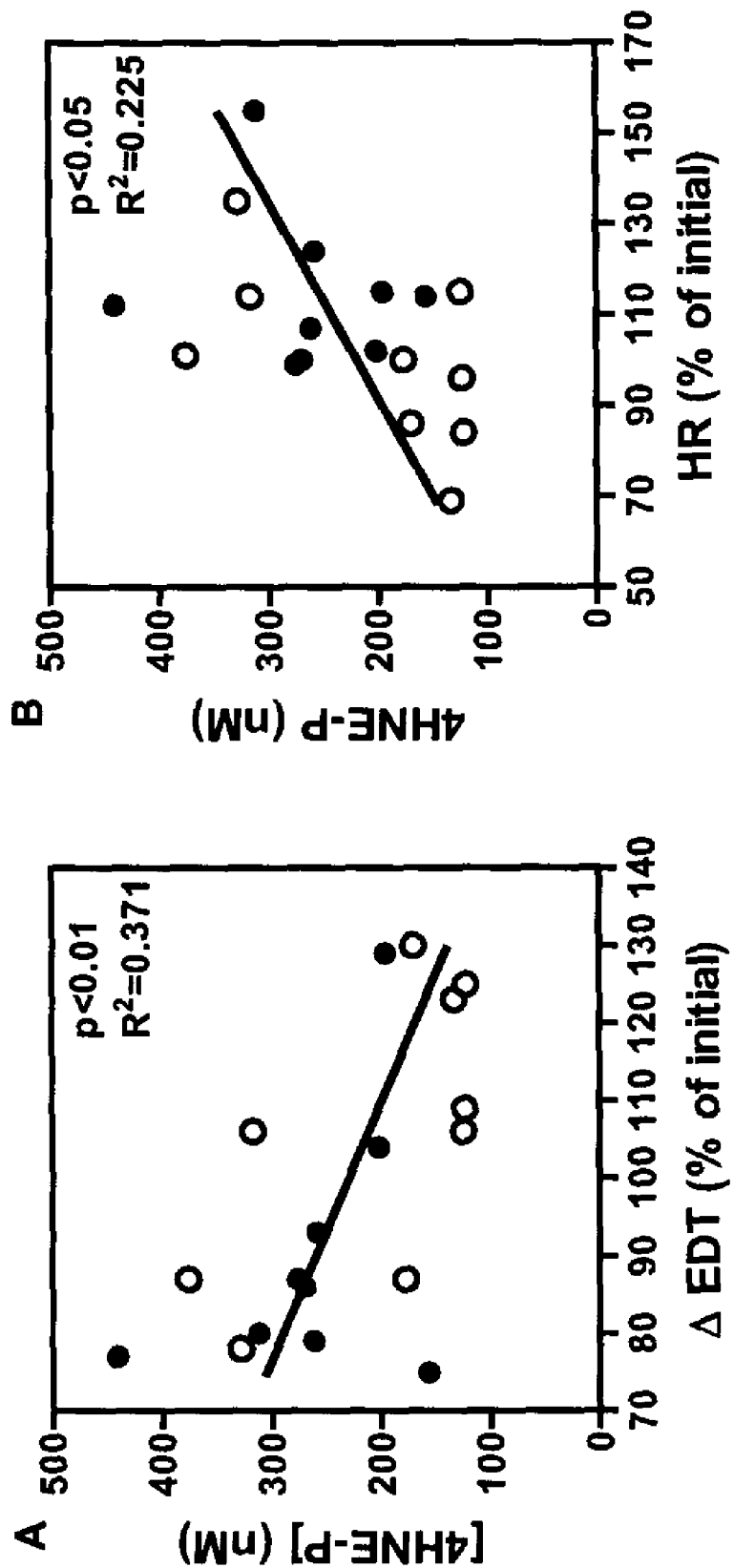
FIG. 9, in X-Y graphs, illustrates correlations between circulating HNE-P and both deterioration of diastolic function (as reflected by EDT) (A) and increased heart rate (B) in SHR after receiving Probucol (•) or vehicle (○) during 4 weeks.

During the 4-week treatment, SHR from both groups depicted a similar 7-8% increase in body weight and systolic blood pressure (V: 7.6±0.2, P: 7.9±0.7; and V: 8.2±2.4, P: 8.3±2.0%, respectively; $p \leq 0.05$). However, SHR receiving vehicle depicted a worsening of indexes of diastolic function. Changes in (i) EDT (decreased; FIG. 9A) and EDR (increased; 18±6%; $p \leq 0.05$) reflect a loss of LV compliance or increased stiffness, while those in (ii) Vp (decreased; FIG. 9B) and IVRTc (increased: 8.9±7.0%; $p \leq 0.05$) indicate impaired LV relaxation. Heart rate was also increased by 20% (FIG. 9C). All these detrimental functional changes were not observed in the Probucol group. In this group, LV diastolic function was preserved, resulting in diminished LA structural and functional remodeling; this is reflected by changes in LADd (decreased: −17.9±6.4%; $p \leq 0.05$) and LAFS (increased; 16.1±5.4%; $p \leq 0.05$).

Circulating HNE-P.

Figure 8:
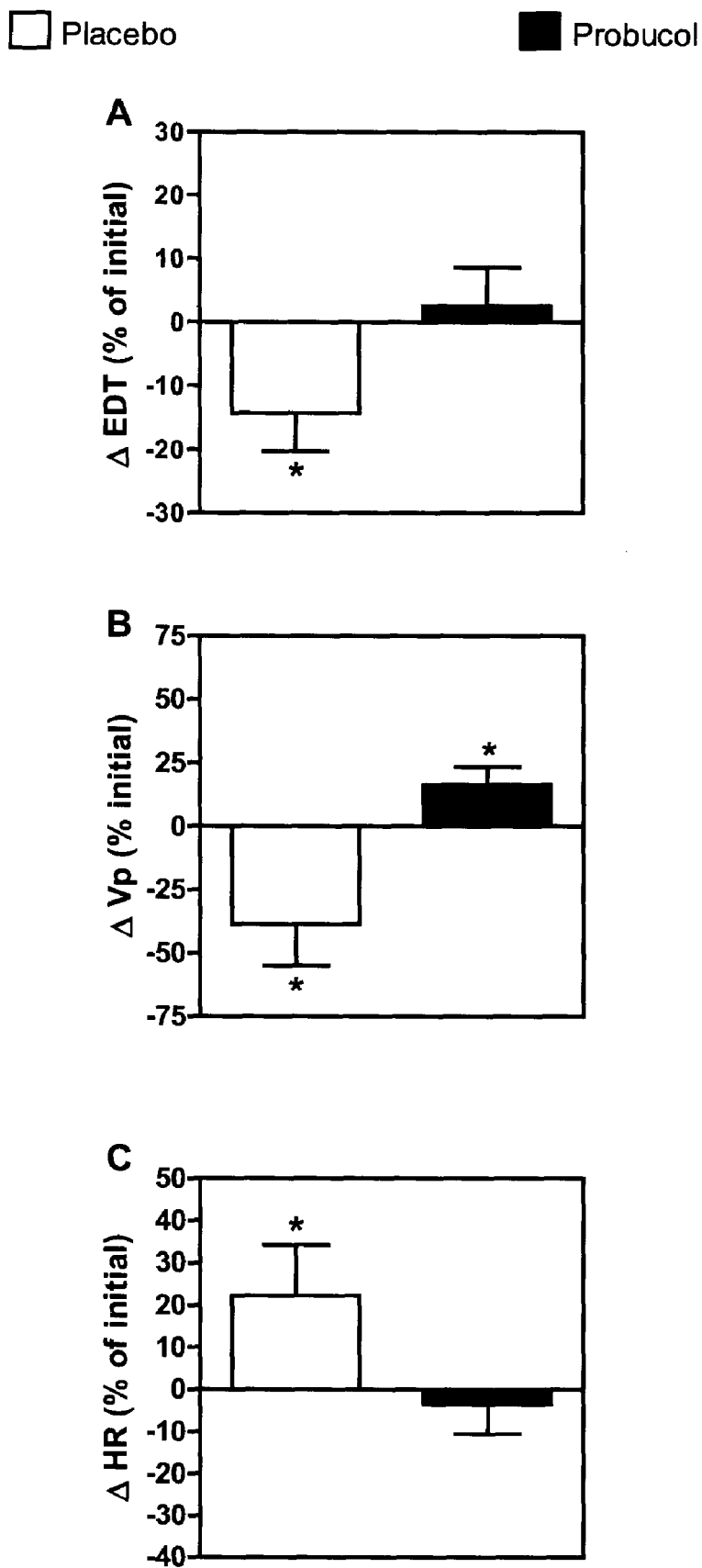
FIG. 8, in bar charts, illustrates changes in diastolic function (panels A &B) and heart rate (panel C) in SHR after receiving Probucol or vehicle during 4 weeks; diastolic dysfunction is reflected by a decrease in indexes of LV compliance (EDT: E wave deceleration time) and relaxation (Vp: mitral flow propagation velocity; results are depicted as percent of pre-treatment values; effect of treatment: *p<0.05.

Circulating HNE-P, which was assessed at the end of treatment in 22-wk-old SHR correlated with indexes of diastolic dysfunction (EDR: $R2=0.518$, $p<0.001$; EDT: $R2=0.371$, $p<0.01$ (FIG. 8A)) and with heart rate (FIG. 8B). Probucol treatment lowered median [min-max] (P: 170.5 [122.5-376.0]; V: 261.3 [157.0-441.5]) and mean (P: 208.2±34.1; V: 263.8±27.4) values of circulating HNE-P by 35% and 21%, respectively ($p=0.1$).

Discussion

In this example, the link between circulating HNE-P levels and cardiac function, was examined in SHR and the impact of Probucol treatment was tested. 18-22-wk-old SHR were used based on finding of high circulating HNE-P in these rats at this age (55 and Example 1). At 18-22 wks of age, the SHR is hypertensive and depicts a compensated cardiac hypertrophy (64). The finding of a worsening of diastolic function in 18-wk-old SHR receiving vehicle for 4 weeks concurs with data from Slama et al. (2004) (63). In this study, treatment of SHR with Probucol attenuated the deterioration of diastolic function and improved left atrial function, an effect that was independent of blood pressure.

Circulating HNE-P levels, which were assessed at the end of treatment, correlated positively with deterioration of diastolic function in SHR, specifically reduction of LV compliance. Furthermore, a positive correlation between circulating HNE-P and increased heart rate was observed. Increased heart rate is factor that has been linked with morbidity and mortality in patients with coronary artery disease (68). Recently, a correlation was reported between immunohistochemically determined HNE-protein adducts in the right ventricle of patients with hypertrophic cardiomyopathy and indexes of cardiac dysfunction (69). Probucol decreased circulating HNE-P levels, but only a relatively small statistical significance was observed for this result. It is hypothesized that this resulted from a type II error given the small number of animals in each group.

The correlation data presented hereinabove suggest a potential role of HNE in the pathogenesis of diastolic dysfunction and in the regulation of heart rate in SHR. A hypothetical mechanism that may explain this results is presented hereinbelow. Isolated hearts exposed to HNE depict vasodilation, reduction of systolic function and contractile failure (70). In isolated rat ventricular myocytes, HNE exerts proarrhythmic effects possibly due to modification of cysteine residues from ion channel proteins (71). It can also depress contraction, possibly through mitogen-activated protein kinase activation (72). Among many potential pathogenic mechanisms, one that appears to have specific relevance to this study is fibrosis. This process appears to be a determinant of LV stiffness, including in SHR (73-75), which could be activated by HNE through TGFb1 signaling (53), but reduced by Probucol (65).

In summary, the results of this example show that left ventricular diastolic function worsens in control SHR from 18 to 22 weeks, leading to a restrictive pattern of diastolic dysfunction, which can be improved by Probucol treatment. The observed correlations between HNE-P and both diastolic dysfunction and heart rate provide additional evidence supporting a role for this aldehyde in the pathophysiological events linked to disease progression in SHR. Ultimately, circulating HNE-P may be correlated with specific pathogenic events that could then become a target for antioxidant therapy.

Human Example

Example 5

The blood levels of HNE-protein adduct was assessed as described hereinabove in 71 human subjects suffering from chronic heart failure. The HNE-protein concentrations averaged 214±67 nM. The levels were correlated to the New York Heart Association Class ($R^2=0.33$; $p<0.05$), suggesting its association with disease severity.

Although the present invention has been described hereinabove by way of preferred embodiments thereof, it can be modified without departing from the spirit, scope and nature of the subject invention, as defined in the appended claims.

LIST OF REFERENCES (1) Gutteridge, J. M.; Halliwell, B. Free radicals and antioxidants in the year 2000. A historical look to the future. Ann. N.Y. Acad. Sci. 899:136-147; 2000.

(2) Leitinger, N. Oxidized phospholipids as modulators of inflammation in atherosclerosis. Curr. Opin. Lipidol. 14:421-430; 2003.

(3) Uchida, K. Role of reactive aldehyde in cardiovascular diseases. Free Radic. Biol. Med. 28:1685-1696; 2000.

(4) Meagher, E. A. Treatment of atherosclerosis in the new millennium: is there a role for vitamin E? Prev. Cardiol. 6:85-90; 2003.

(5) Kritharides, L.; Stocker, R. The use of antioxidant supplements in coronary heart disease. Atherosclerosis 164:211-219; 2002.

(6) Lonn, E.; Bosch, J.; Yusuf, S.; Sheridan, P.; Pogue, J.; Arnold, J. M.; Ross, C.; Arnold, A.; Sleight, P.; Probstfield, J.; Dagenais, G. R. Effects of long-term vitamin E supplementation on cardiovascular events and cancer: a randomized controlled trial. JAMA 293:1338-1347; 2005.

(7) Kadiiska, M. B.; Gladen, B. C.; Baird, D. D.; Germolec, D.; Graham, L. B.; Parker, C. E.; Nyska, A.; Wachsman, J. T.; Ames, B. N.; Basu, S.; Brot, N.; FitzGerald, G. A.; Floyd, R. A.; George, M.; Heinecke, J. W.; Hatch, G. E.; Hensley, K.; Lawson, J. A.; Marnett, L. J.; Morrow, J. D.; Murray, D. M.; Plastaras, J.; Roberts, L. J.; Rokach, J.; Shigenaga, M. K.; Sohal, R. S.; Sun, J.; Tice, R. R.; Van Thiel, D. H.; Weliner, D.; Walter, P. B.; Tomer, K. B.; Mason, R. P.; Barrett, J. C. Biomarkers of oxidative stress study II: are oxidation products of lipids, proteins, and DNA markers of CCl4 poisoning? Free Radic. Biol. Med. 38:698-710; 2005.

(8) Moore, K.; Roberts, L. J. Measurement of lipid peroxidation. Free Radic. Res. 28:659-671; 1998.

(9) Halliwell, B.; Whiteman, M. Measuring reactive species and oxidative damage in vivo and in cell culture: how should you do it and what do the results mean? Br. J. Pharmacol. 142:231-255; 2004.

(10) Zarkovic, N. 4-hydroxynonenal as a bioactive marker of pathophysiological processes. Mol. Aspects. Med. 24:281-291; 2003.

(11) Esterbauer, H.; Schaur, R. J.; Zollner, H. Chemistry and biochemistry of 4-hydroxynonenal, malonaldehyde and related aldehydes. Free Radic. Biol. Med. 11:81-128; 1991.

(12) Awasthi, Y. C.; Sharma, R.; Cheng, J. Z.; Yang, Y.; Sharma, A.; Singhal, S. S.; Awasthi, S. Role of 4-hydroxynonenal in stress-mediated apoptosis signaling. Mol. Aspects. Med. 24:219-230; 2003.

(13) Poli, G.; Schaur, R. J. 4-Hydroxynonenal in the pathomechanisms of oxidative stress. IUBMB. Life 50:315-321; 2000.

(14) Schaur, R. J. Basic aspects of the biochemical reactivity of 4-hydroxynonenal. Mol. Aspects. Med 24:149-159; 2003.

(15) Gueraud, F.; Peiro, G.; Bernard, H.; Alary, J.; Creminon, C.; Debrauwer, L.; Rathahao, E.; Drumare, M. F.; Canlet, C.; Wal, J. M.; Bories, G. Enzyme immunoassay for a urinary metabolite of 4-hydroxynonenal as a marker of lipid peroxidation. Free Radic. Biol. Med. 40:54-62; 2006.

(16) Volkel, W.; Alvarez-Sanchez, R.; Weick, I.; Mally, A.; Dekant, W.; Pahler, A. Glutathione conjugates of 4-hydroxy-2(E)-nonenal as biomarkers of hepatic oxidative stress-induced lipid peroxidation in rats. Free Radic. Biol. Med. 38:1526-1536; 2005.

(17) Eaton, P.; Li, J. M.; Hearse, D. J.; Shattock, M. J. Formation of 4-hydroxy-2-nonenal-modified proteins in ischemic rat heart. Am. J. Physiol 276:H935-H943; 1999.

(18) Veronneau, M.; Comte, B.; Des Rosiers C. Quantitative gas chromatographic-mass spectrometric assay of 4-hydroxynonenal bound to thiol proteins in ischemic/reperfused rat hearts. Free Radic. Biol. Med. 33:1380-1388; 2002.

(19) Benderdour, M.; Charron, G.; Comte, B.; Ayoub, R.; Beaudry, D.; Foisy, S.; Deblois, D.; Des Rosiers C. Decreased cardiac mitochondrial NADP+-isocitrate dehydrogenase activity and expression: a marker of oxidative stress in hypertrophy development. Am. J. Physiol Heart Circ. Physiol 287:H2122-H2131; 2004.

(20) Nakamura, R.; Egashira, K.; Machida, Y.; Hayashidani, S.; Takeya, M.; Utsumi, H.; Tsutsui, H.; Takeshita, A. Probucol attenuates left ventricular dysfunction and remodeling in tachycardia-induced heart failure: roles of oxidative stress and inflammation. Circulation 106:362-367; 2002.

(21) Toyokuni, S.; Yamada, S.; Kashima, M.; Ihara, Y.; Yamada, Y.; Tanaka, T.; Hiai, H.; Seino, Y.; Uchida, K. Serum 4-hydroxy-2-nonenal-modified albumin is elevated in patients with type 2 diabetes mellitus. Antioxid. Redox. Signal. 2:681-685; 2000.

(22) Salomon, R. G.; Kaur, K.; Podrez, E.; Hoff, H. F.; Krushinsky, A. V.; Sayre, L. M. HNE-derived 2-pentylpyrroles are generated during oxidation of LDL, are more prevalent in blood plasma from patients with renal disease or atherosclerosis, and are present in atherosclerotic plaques. Chem. Res. Toxicol. 13:557-564; 2000.

(23) Cabassi, A.; Dumont, E. C.; Girouard, H.; Bouchard, J. F.; Le Jossec, M.; Lamontagne, D.; Besner, J. G.; de Champlain, J. Effects of chronic N-acetylcysteine treatment on the actions of peroxynitrite on aortic vascular reactivity in hypertensive rats. J. Hypertens. 19:1233-1244; 2001.

(24) Yuan, Y. V.; Kitts, D. D. Dietary (n-3) fat and cholesterol alter tissue antioxidant enzymes and susceptibility to oxidation in SHR and WKY rats. J. Nutr. 133:679-688; 2003.

(25) Kobayashi, N.; DeLano, F. A.; Schmid-Schonbein, G. W. Oxidative stress promotes endothelial cell apoptosis and loss of microvessels in the spontaneously hypertensive rats. Arterioscler. Thromb. Vasc. Biol. 25:2114-2121; 2005.

(26) Wang, X.; Desai, K.; Chang, T.; Wu, L. Vascular methylglyoxal metabolism and the development of hypertension. J. Hypertens. 23:1565-1573; 2005.

(27) Cosentino, F.; Patton, S.; d'Uscio, L. V.; Werner, E. R.; Werner-Felmayer, G.; Moreau, P.; Malinski, T.; Luscher, T. F. Tetrahydrobiopterin alters superoxide and nitric oxide release in prehypertensive rats. J. Clin. Invest 101:1530-1537; 1998.

(28) Bradford, M. M. A rapid and sensitive method for the quantitation of microgram quantities of protein utilizing the principle of protein-dye binding. Anal. Biochem. 72:248-254; 1976.

(29) Des Rosiers C.; Rivest, M. J.; Boily, M. J.; Jette, M.; Carrobe-Cohen, A.; Kumar, A. Gas chromatographic-mass spectrometric assay of tissue malondialdehyde, 4-hydroxynonenal, and other aldehydes after their reduction to stable alcohols. Anal. Biochem. 208:161-170; 1993.

(30) Morrow, J. D. The isoprostanes: their quantification as an index of oxidant stress status in vivo. Drug Metab Rev. 32:377-385; 2000.

(31) Tsikas, D.; Schwedhelm, E.; Stutzer, F. K.; Gutzki, F. M.; Rode, I.; Mehls, C.; Frolich, J. C. Accurate quantification of basal plasma levels of 3-nitrotyrosine and 3-nitrotyrosinoalbumin by gas chromatography-tandem mass spectrometry. J. Chromatogr. B Analyt. Technol. Biomed. Life Sci. 784:77-90; 2003.

(32) Strohmaier, H.; Hinghofer-Szalkay, H.; Schaur, R. J. Detection of 4-hydroxynonenal (HNE) as a physiological component in human plasma. J. Lipid Mediat. Cell Signal. 11:51-61; 1995.

(33) Spies-Martin, D.; Sommerburg, O.; Langhans, C. D.; Leichsenring, M. Measurement of 4-hydroxynonenal in small volume blood plasma samples: modification of a gas chromatographic-mass spectrometric method for clinical settings. J. Chromatogr. B Analyt. Technol. Biomed. Life Sci. 774:231-239; 2002.

(34) Uchida, K.; Stadtman, E. R. Selective cleavage of thioether linkage in proteins modified with 4-hydroxynonenal. Proc. Natl. Acad. Sci. U.S.A. 89:5611-5615; 1992.

(35) Bruenner, B. A.; Jones, A. D.; German, J. B. Direct characterization of protein adducts of the lipid peroxidation product 4-hydroxy-2-nonenal using electrospray mass spectrometry. Chem. Res. Toxicol. 8:552-559; 1995.

(36) Kinter, M.; Robinson, C. S.; Grimminger, L. C.; Gillies, P. J.; Shimshick, E. J.; Ayers, C. Whole blood and plasma concentrations of 4-hydroxy-2-nonenal in Watanabe heritable hyperlipidemic versus New Zealand White rabbits. Biochem. Biophys. Res. Commun. 199:671-675; 1994.

(37) Oliver, C. N.; Ahn, B. W.; Moerman, E. J.; Goldstein, S.; Stadtman, E. R. Age-related changes in oxidized proteins. J. Biol. Chem. 262:5488-5491; 1987.

(38) Gillery, P.; Bordas-Fonfrede, M.; Chapelle, J. P.; Drouin, P.; Hue, G.; Levy-Marchal, C.; Perier, C.; Selam, J. L.; Slama, G.; Thivolet, C.; Vialettes, B. HBA1c: clinical and biological agreement for standardization of assay methods. Report by the experts of ALFEDIAM (Association de Langue Francaise pour lEtude du Diabete et des Maladies Metabolique) and SFBC (Societe Francaise de Biologie Clinique)). Diabetes Metab 25:283-287; 1999.

(39) Selley, M. L. (E)-4-hydroxy-2-nonenal may be involved in the pathogenesis of Parkinson's disease. Free Radic. Biol. Med. 25:169-174; 1998.

(40) Musiek, E. S.; Cha, J. K.; Yin, H.; Zackert, W. E.; Terry, E. S.; Porter, N. A.; Montine, T. J.; Morrow, J. D. Quantification of F-ring isoprostane-like compounds (F(4)-neuroprostanes) derived from docosahexaenoic acid in vivo in humans by a stable isotope dilution mass spectrometric assay. J Chromatogr. B Analyt. Technol. Biomed. Life Sci. 799:95-102; 2004.

(41) Nonaka-Sarukawa, M.; Yamamoto, K.; Aoki, H.; Takano, H.; Katsuki, T.; Ikeda, U.; Shimada, K. Increased urinary 15-F2t-isoprostane concentrations in patients with non-ischaemic congestive heart failure: a marker of oxidative stress. Heart 89:871-874; 2003.

(42) Schwedhelm, E.; Bartling, A.; Lenzen, H.; Tsikas, D.; Maas, R.; Brummer, J.; Gutzki, F. M.; Berger, J.; Frolich, J. C.; Boger, R. H. Urinary 8-iso-prostaglandin F2alpha as a risk marker in patients with coronary heart disease: a matched case-control study. Circulation 109:843-848; 2004.

(43) Gaut, J. P.; Byun, J.; Tran, H. D.; Heinecke, J. W. Artifact-free quantification of free 3-chlorotyrosine, 3-bromotyrosine, and 3-nitrotyrosine in human plasma by electron capture-negative chemical ionization gas chromatography mass spectrometry and liquid chromatography-electrospray ionization tandem mass spectrometry. Anal. Biochem. 300: 252-259; 2002.

(44) Shishehbor, M. H.; Aviles, R. J.; Brennan, M. L.; Fu, X.; Goormastic, M.; Pearce, G. L.; Gokce, N.; Keaney, J. F., Jr.; Penn, M. S.; Sprecher, D. L.; Vita, J. A.; Hazen, S. L. Association of nitrotyrosine levels with cardiovascular disease and modulation by statin therapy. JAMA 289:1675-1680; 2003.

(45) Siems, W.; Grune, T. Intracellular metabolism of 4-hydroxynonenal. Mol. Aspects. Med 24:167-175; 2003.

(46) Doggrell, S. A.; Brown, L. Rat models of hypertension, cardiac hypertrophy and failure. Cardiovasc. Res. 39:89-105; 1998.

(47) Shimamoto, N.; Goto, N.; Tanabe, M.; Imamoto, T.; Fujiwara, S.; Hirata, M. Myocardial energy metabolism in the hypertrophied hearts of spontaneously hypertensive rats. Basic Res. Cardiol. 77:359-7; 1982.

(48) Diez, J.; Panizo, A.; Hernandez, M.; Vega, F.; Sola, I.; Fortuno, M. A.; Pardo, J. Cardiomyocyte apoptosis and cardiac angiotensin-converting enzyme in spontaneously hypertensive rats. Hypertension 30:1029-1034; 1997.

(49) Reckelhoff, J. F.; Romero, J. C. Role of oxidative stress in angiotensin-induced hypertension. Am. J. Physiol Regul. Integr. Comp Physiol 284:R893-R912; 2003.

(50) Srivastava, S.; Dixit, B. L.; Cai, J.; Sharma, S.; Hurst, H. E.; Bhatnagar, A.; Srivastava, S. K. Metabolism of lipid peroxidation product, 4-hydroxynonenal (HNE) in rat erythrocytes: role of aldose reductase. Free Radic. Biol. Med. 29:642-651; 2000.

(51) Esterbauer H, Schaur R J, Zollner H. Chemistry and biochemistry of 4-hydroxynonenal, malonaldehyde and related aldehydes. Free Radic Biol Med 1991; 11(1):81-128.

(52) Zarkovic N. 4-hydroxynonenal as a bioactive marker of pathophysiological processes. Mol Aspects Med 2003; 24(4-5):281-291.

(53) Poli G, Schaur R J. 4-Hydroxynonenal in the pathomechanisms of oxidative stress. IUBMB Life 2000; 50(4-5): 315-321.

(54) Uchida K. Role of reactive aldehyde in cardiovascular diseases. Free Radic Biol Med 2000; 28(12):1685-1696.

(55) Asselin C, Bouchard B, Tardif J C, Des Rosiers C. Circulating 4-hydroxynonenal-protein thioether adducts assessed by gas chromatography-mass spectrometry are increased with disease progression and aging in spontaneously hypertensive rats. Free Radic Biol Med 2006; 41(1):97-105.

(56) Benderdour M, Charron G, Deblois D, Comte B, Des Rosiers C. Cardiac mitochondrial NADP+-isocitrate dehydrogenase is inactivated through 4-hydroxynonenal adduct formation: an event that precedes hypertrophy development. J Biol Chem 2003; 278(46):45154-45159.

(57) Benderdour M, Charron G, Comte B et al. Decreased cardiac mitochondrial NADP+-isocitrate dehydrogenase activity and expression: a marker of oxidative stress in hypertrophy development. Am J Physiol Heart Circ Physiol 2004; 287(5):H2122-H2131.

(58) Chiappe De Cingolani G E, Caldiz C I. Insulin resistance and GLUT-4 glucose transporter in adipocytes from hypertensive rats. Metabolism 2004; 53(3):382-387.

(59) Shimamoto N, Goto N, Tanabe M, Imamoto T, Fujiwara S, Hirata M. Myocardial energy metabolism in the hypertrophied hearts of spontaneously hypertensive rats. Basic Res Cardiol 1982; 77(4):359-7.

(60) Cosentino F, Patton S, d'Uscio L V, Werner E R, Werner-Felmayer G, Moreau P et al. Tetrahydrobiopterin alters superoxide and nitric oxide release in prehypertensive rats. J Clin Invest 1998; 101(7):1530-1537.

(61) Cabassi A, Dumont E C, Girouard H, Bouchard J F, Le Jossec M, Lamontagne D et al. Effects of chronic N-acetylcysteine treatment on the actions of peroxynitrite on aortic vascular reactivity in hypertensive rats. J Hypertens 2001; 19(7):1233-1244.

(62) Tardif J C, Gregoire J, Schwartz L, et al, for the Canadian Antioxidant Restenosis Trial (CART-1) Investigators. Effects of AGI-1067 and Probucol after percutaneous coronary interventions. Circulation 2003; 107:552-558.

(63) Slama M, Ahn J, Varagic J, Susic D, Frohlich E D. Long-term left ventricular echocardiographic follow-up of SHR and WKY rats: effects of hypertension and age. Am J Physiol Heart Circ Physiol 2004; 286(1):H181-H185.

(64) Kohno I, Honma H, Nakamura T, Tamura K. Comparison of blood pressure, heart rate and activity between normotensive and spontaneously-hypertensive rats. Chronobiologia 1994; 21(1-2):45-56.

(65) Nakamura R, Egashira K, Machida et al. Probucol attenuates left ventricular dysfunction and remodeling in

(66) Lou H, Danelisen I, Singal P K. Involvement of mitogen-activated protein kinases in adriamycin-induced cardiomyopathy. Am J Physiol Heart Circ Physiol 2005; 288(4): H1925-H1930.

(67) Sia Y T, Lapointe N, Parker T G et al. Beneficial effects of long-term use of the antioxidant Probucol in heart failure in the rat. Circulation 2002; 105(21):2549-2555.

(68) Diaz A, Bourassa M G, Guertin M C, Tardif J C. Long-term prognostic value of resting heart rate in patients with suspected or proven coronary artery disease. Eur Heart J 2005; 26(10):967-974.

(69) Nakamura K, Kusano K F, Matsubara H et al. Relationship between oxidative stress and systolic dysfunction in patients with hypertrophic cardiomyopathy. J Card Fail 2005; 11 (2):117-123.

(70) Ishikawa T, Esterbauer H, Sies H. Role of cardiac glutathione transferase and of the glutathione S-conjugate export system in biotransformation of 4-hydroxynonenal in the heart. J Biol Chem 1986; 261(4):1576-1581.

(71) Bhatnagar A. Electrophysiological effects of 4-hydroxynonenal, an aldehydic product of lipid peroxidation, on isolated rat ventricular myocytes. Circ Res 1995; 76(2):293-304.

(72) Aberle N S, Picklo M J, Sr., Amarnath V, Ren J. Inhibition of cardiac myocyte contraction by 4-hydroxy-trans-2-nonenal. Cardiovasc Toxicol 2004; 4(1):21-28.

(73) Ahn J, Varagic J, Slama M, Susic D, Frohlich E D. Cardiac structural and functional responses to salt loading in SHR. Am J Physiol Heart Circ Physiol 2004; 287(2):H767-H772.

(74) Brilla C G, Matsubara L, Weber K T. Advanced hypertensive heart disease in spontaneously hypertensive rats. Lisinopril-mediated regression of myocardial fibrosis. Hypertension 1996; 28(2):269-275.

(75) Gagnon C, Legault F, Geraldes P, Tanguay J F, Lambert C. Diverse effects of Ace inhibitors and angiotensin 11 receptor antagonists on prevention of cardiac hypertrophy and collagen distribution in spontaneously hypertensive rats. Int J Cardiol 2004; 97(3):373-381.

(76) Burcham, P. C.; Kaminskas, L. M.; Fontaine, F. R.; Petersen, D. R.; Pyke, S. M. Aldehyde-sequestering drugs: tools for studying protein damage by lipid peroxidation products. Toxicology 181-182:229-236; 2002.

All references cited and/or discussed in this specification are incorporated herein by reference in their entirety and to the same extent as if each reference was individually incorporated by reference.

What is claimed is:

1. A method for detecting oxidative stress using a biological sample, comprising:
 (a) obtaining the biological sample comprising a biomarker of oxidative stress having a measurable component, said biological sample being selected from whole blood, blood derivatives, and combinations thereof;
 (b) chemically stabilizing the biomarker in the sample;
 (c) isolating the measurable component;
 (d) extracting the measurable component; and
 (e) measuring the quantity of the measurable component.

2. The method of claim 1, wherein the biomarker of oxidative stress is selected from an aldehyde-protein adduct and an aldehyde metabolite-protein adduct.

3. The method of claim 2, wherein the aldehyde is 4-hydroxy-2,3-nonenal (HNE).

4. The method of claim 2, wherein the aldehyde metabolite is 1,4-dihydroxynonene (DHN).

5. The method of claim 1, wherein the measurable component is selected from DHN and [$^2$H]DHN.

6. The method of claim 2, comprising chemically stabilizing the biomarker in the sample by reducing the aldehyde to its alcohol.

7. The method of claim 6, wherein the step of reducing the aldehyde to its alcohol comprises adding one of $NaBH_4$ and $NaB^2H_4$ to the biological sample.

8. The method of claim 3, wherein the step of reducing the aldehyde to its alcohol comprises reducing HNE to DHN and/or reducing HNE to its deuterated alcohol [$^2$H]DHN.

9. The method of claim 1, wherein the biological sample contains molecules selected from HNE, HNE-protein adducts, DHN, DHN-protein adducts, metabolites of HNE, and combinations thereof.

10. The method of claim 1, comprising isolating the measurable component by cleaving a protein linkage.

11. The method of claim 10, wherein the step of cleaving a protein linkage comprises cleaving a protein thioether linkage using Raney nickel catalysis.

12. The method of claim 11, wherein the Raney nickel catalysis is conducted for about 5 to about 20 hours at a temperature of about 45° C. to about 60° C.

13. The method of claim 1, wherein the measurable component of the biomarker of oxidative stress is a metabolite produced by peroxidation of fatty acids.

14. The method of claim 1, wherein the measurable component of the biomarker of oxidative stress is selected from: 4-hydroxynonenal, 4-oxononenal, 4-hydroxyhexenal and 4-oxohexenal.

15. The method of claim 1, wherein the blood derivatives are selected from plasma, albumin, and oxidized lipoprotein at least one of blood and a blood derivative.

16. The method of claim 1, wherein the quantity of the measurable component is measured using gas chromatography coupled to mass spectrometry.

* * * * *